United States Patent
Ohodnicki, Jr. et al.

(10) Patent No.: US 8,638,440 B1
(45) Date of Patent: Jan. 28, 2014

(54) PLASMONIC TRANSPARENT CONDUCTING METAL OXIDE NANOPARTICLES AND FILMS FOR OPTICAL SENSING APPLICATIONS

(71) Applicants: Paul R. Ohodnicki, Jr., Alison Park, PA (US); Congjun Wang, Bethel Park, PA (US); Mark A. Andio, Pittsburgh, PA (US)

(72) Inventors: Paul R. Ohodnicki, Jr., Alison Park, PA (US); Congjun Wang, Bethel Park, PA (US); Mark A. Andio, Pittsburgh, PA (US)

(73) Assignee: U.S. Department of Energy, Washington, DC (US)

( * ) Notice: Subject to any disclaimer, the term of this patent is extended or adjusted under 35 U.S.C. 154(b) by 0 days.

(21) Appl. No.: 13/927,223

(22) Filed: Jun. 26, 2013

Related U.S. Application Data

(60) Provisional application No. 61/664,886, filed on Jun. 27, 2012, provisional application No. 61/762,426, filed on Feb. 8, 2013.

(51) Int. Cl.
*G01N 21/00* (2006.01)
*G01N 21/55* (2006.01)

(52) U.S. Cl.
USPC .......................................... 356/437; 356/445

(58) Field of Classification Search
USPC .............. 356/432–448, 246; 250/343, 548.1; 436/134, 167, 168; 422/88, 91, 94, 83, 422/68.1
See application file for complete search history.

(56) References Cited

U.S. PATENT DOCUMENTS

| | | | | |
|---|---|---|---|---|
| 4,355,997 | A * | 10/1982 | Smith et al. ..................... | 436/25 |
| 5,338,515 | A * | 8/1994 | Dalla Betta et al. ............. | 422/95 |
| 5,580,793 | A * | 12/1996 | Wanner ........................ | 436/144 |
| 5,941,068 | A * | 8/1999 | Brown et al. .................. | 60/297 |
| 7,249,564 | B2 * | 7/2007 | Lissianski et al. ............. | 110/345 |
| 7,864,322 | B2 * | 1/2011 | Carpenter et al. ............ | 356/437 |

(Continued)

OTHER PUBLICATIONS

Ando, "Recent advances in optochemical sensors for the detection of H2, O2, O3, CO, CO2 and H2O in air," Trends in Analytical Chemistry 25(10) (2006).

(Continued)

*Primary Examiner* — Sang Nguyen
(74) *Attorney, Agent, or Firm* — James B. Potts; Brian J. Lally; John T. Lucas

(57) ABSTRACT

The disclosure relates to a method of detecting a change in a chemical composition by contacting a doped oxide material with a monitored stream, illuminating the doped oxide material with incident light, collecting exiting light, monitoring an optical signal based on a comparison of the incident light and the exiting light, and detecting a shift in the optical signal. The doped metal oxide has a carrier concentration of at least $10^{18}/cm^3$, a bandgap of at least 2 eV, and an electronic conductivity of at least $10^1$ S/cm, where parameters are specified at a temperature of 25° C. The optical response of the doped oxide materials results from the high carrier concentration of the doped metal oxide, and the resulting impact of changing gas atmospheres on that relatively high carrier concentration. These changes in effective carrier densities of conducting metal oxide nanoparticles are postulated to be responsible for the change in measured optical absorption associated with free carriers. Exemplary doped metal oxides include but are not limited to Al-doped ZnO, Sn-doped $In_2O_3$, Nb-doped $TiO_2$, and F-doped $SnO_2$.

20 Claims, 13 Drawing Sheets

(56) References Cited

U.S. PATENT DOCUMENTS

| | | | |
|---|---|---|---|
| 8,308,848 B1* | 11/2012 | Alptekin et al. | 95/136 |
| 8,411,275 B1* | 4/2013 | Ohodnicki et al. | 356/445 |
| 2003/0134426 A1* | 7/2003 | Jiang et al. | 436/121 |
| 2004/0112743 A1* | 6/2004 | Fukatsu et al. | 204/424 |
| 2006/0060815 A1* | 3/2006 | Punnoose | 252/62.56 |
| 2006/0193557 A1* | 8/2006 | Bradley et al. | 385/32 |
| 2009/0207413 A1* | 8/2009 | Carpenter et al. | 356/437 |
| 2009/0218235 A1* | 9/2009 | McDonald et al. | 205/775 |
| 2010/0210029 A1* | 8/2010 | Meinhart et al. | 436/168 |
| 2011/0038784 A1* | 2/2011 | Plata et al. | 423/447.1 |
| 2011/0152070 A1* | 6/2011 | Fansler et al. | 502/183 |

OTHER PUBLICATIONS

Korotcenkov, "Metal oxides for solid-state gas sensors: What determines our choice?," Materials Science and Engineering B 139 (2007).

Schleunitz et al., "Optical gas sensitivity of a metal oxide multilayer system with gold-nano-clusters," Sensors and Actuators B 127 (2007).

Gaspera et al., "CO optical sensing properties of nanocrystalline ZnO—Au films: Effect of doping with transition metal ions," Sensors and Actuators B 161 (2012).

Gaspera et al., "Enhanced optical and electrical gas sensing response of sol-gel based NiO—Au and ZnO—Au nanostructured thin films," Sensors and Actuators B 164 (2012).

Ando et al., "Combined effects of small gold particles on the optical gas sensing by transition metal oxide films," Catalysis Today 36 (1997).

Remmel et al., "Investigation on nanocrystalline copper-doped zirconia thin films for optical sensing of carbon monoxide at high temperature," Sensors and Actuators B 160 (2011).

Ohodnicki et al., "Plasmonic Transparent Conducting Metal Oxide Nanoparticles and Nanoparticle Films for Optical Sensing Applications," Thin Solid Films (2013), doi: 10.1016/j.tsf.2013.04.145.

Cimitan et al., "Solvothermal synthesis and properties control of doped ZnO nanoparticles," Journal of Colloid and Interface Science 329 (2009).

* cited by examiner

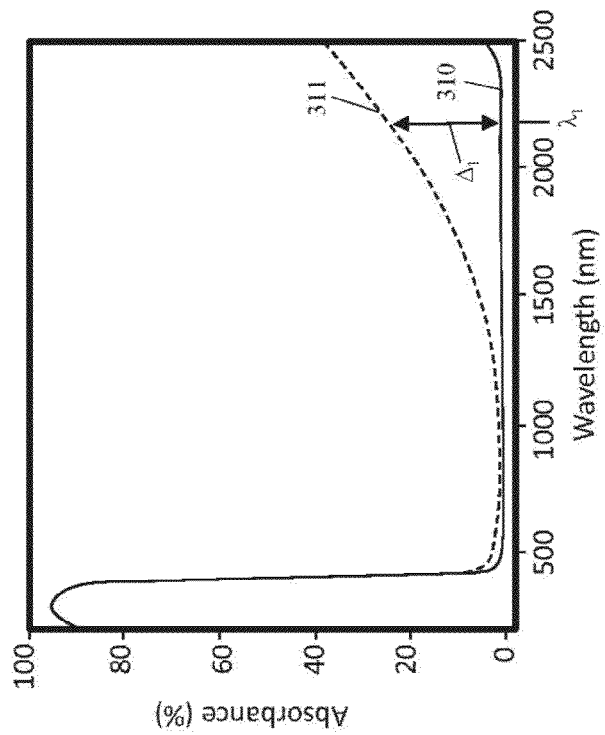
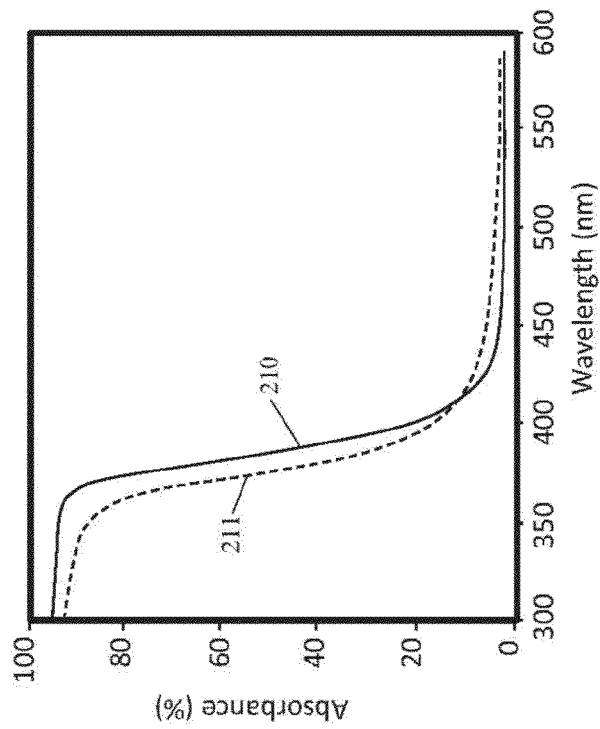
FIG. 3
FIG. 2

PLASMONIC TRANSPARENT CONDUCTING METAL OXIDE NANOPARTICLES AND FILMS FOR OPTICAL SENSING APPLICATIONS

RELATION TO OTHER APPLICATIONS

This patent application claims priority from provisional patent applications 61/664,886 filed Jun. 27, 2012 and 61/762,426 filed Feb. 8, 2013, which are hereby incorporated by reference.

GOVERNMENT INTERESTS

The United States Government has rights in this invention pursuant to the employer-employee relationship of the Government to the inventors as U.S. Department of Energy employees and site-support contractors at the National Energy Technology Laboratory.

FIELD OF THE INVENTION

One or more embodiments relates to a method of detecting a change in a chemical composition by contacting a doped oxide material with a gas stream at a temperature of at least 100° C., illuminating the doped oxide material, and detecting a shift in the optical signal. The doped metal oxide has a carrier concentration of at least $10^{18}/cm^3$, a bandgap of at least 2 eV, and an electronic conductivity of at least $10^1$ S/cm, where parameters are specified at a temperature of 25° C.

BACKGROUND

Improved sensors are needed that can operate in harsh environments for the next generation of technologies for higher efficiency, lower emission fossil-fueled power plants including oxy-fuel combustion processes for carbon capture and sequestration and coal gasification to produce syngas which can be converted to electrical power using solid-oxide fuel cells or gas turbines. Improved harsh environment sensors and controls would also enable significant gains in energy efficiency for the existing fleet of coal-fired power plants and a number of major domestic manufacturing industries. In particular, chemical sensors capable of operating at elevated temperatures in highly reducing, oxidizing, and/or corrosive environments can be leveraged across a broad range of applications including coal gasification, combustion turbines, solid oxide fuel cells, and advanced boiler systems.

Optical sensors are of increasing interest for a wide range of embedded sensing applications due to a number of inherent advantages as compared to other sensor technologies including the ability to monitor several different optical properties of a selected sensing material (transmission, reflection, luminescence). However, an indirect relationship between electrical and optical properties of most metal oxide based films implies that the large body of existing work on semiconducting materials for chemi-resistive based gas sensing applications provides only limited guidance for development of sensor materials for optical sensing applications. Material systems with useful optical responses specifically tailored for the application of interest will therefore be required.

Metal oxides such as $WO_3$ have been utilized as optical sensors for $H_2$ while other metal oxides such as NiO and $Co_3O_4$ have been explored for optical sensing of reducing gases such as CO. However, these materials suffer from limited temperature stability in highly reducing conditions and typical dynamic ranges of measured output signals based on absorbance or reflectance have limited their practical use in a gas sensing instrument. See e.g. Ando, "Recent advances in optochemical sensors for the detection of $H_2$, $O_2$, $O_3$, CO, $CO_2$ and $H_2O$ in air," *Trends in Analytical Chemistry* 25(10) (2006); see also Korotcenkov, "Metal oxides for solid-state gas sensors: What determines our choice?" *Materials Science and Engineering B* 139 (2007). Incorporation of noble metals such as gold nanoparticles into these metal oxides has generally been employed to enable responses that are suitable for practical gas sensing. See e.g., Schleunitz et al., "Optical gas sensitivity of a metal oxide multilayer system with gold-nano-clusters," *Sensors and Actuators B* 127 (2007); see also Gaspera et al., "CO optical sensing properties of nanocrystalline ZnO—Au films: Effect of doping with transition metal ions," *Sensors and Actuators B* 161 (2012); see also Gaspera et al., "Enhanced optical and electrical gas sensing response of sol-gel based NiO—Au and ZnO—Au nanostructured thin films," Sensors and Actuators B 164 (2012); and see Ando et al., "Combined effects of small gold particles on the optical gas sensing by transition metal oxide films" *Catalysis Today* 36 (1997). In other cases, metal oxides such as ZnO with various dopants have been utilized and absorbance changes have been noted for gases such as ammonia, methanol and ethanol, however the mechanism has generally been attributed to the adsorption of oxygen molecules at the metal oxide surface and the dopant was utilized to enhance catalytic activity, and correspondingly measurement temperatures have been limited to below about 10° C. The time constants for the measured responses also tend to be prohibitively long such that they are not practical for a gas sensing device. See e.g., Renganathan et al., "Gas sensing properties of a clad modified fiber optic sensor with Ce, Li and Al doped nanocrystalline zinc oxides," *Sensors and Actuators B* 156 (2011). Dopants such as CuO have also been employed with metal oxides such as $ZrO_2$ in order to provide sensing through reversible red-ox reactions, however such approaches can suffer from instability under high temperature and/or high reducing agent concentrations. See e.g., Remmel et al., "Investigation on nanocrystalline copper-doped zirconia thin films for optical sensing of carbon monoxide at high temperature," *Sensors and Actuators B* 160 (2011).

Weak dynamic range of optical responses of high temperature stable metal oxides to changing gas atmospheres has generally required investigators to amplify the response by applying them to optical fibers with fiber bragg gratings. By periodically modifying the refractive index of the core of the optical fiber, the interaction with a sensing layer can be enhanced by orders of magnitude. However, fiber bragg gratings exhibit an inherent temperature instability above 50006 regardless of the sensing layer employed and increase the cost and complexity of a sensor device. See e.g. Tang et al., "Acidic ZSM-5 zeolite-coated long period fiber grating for optical sensing of ammonia," *J. Mater. Chem.* 21 (2011); see also Jiang et al., "Multilayer fiber optic sensors for in situ gas monitoring in harsh environments," *Sensors and Actuators B* 177 (2013); see also Wei et al, "Terbium doped strontium cerate enabled long period fiber gratings for high temperature sensing of hydrogen," *Sensors and Actuators B* 152 (2011); see also Remmel et al., "Investigation n on nanocrystalline copper-doped zirconia thin films for optical sensing of carbon monoxide at high temperature." *Sensors and Actuators B* 160 (2011).

It would be advantageous to provide a method of improving the optical responses of metal oxides to changes in chemical compositions without resort to incorporation of noble metals, such as gold, platinum, and silver and to mitigate the need for advanced sensor designs such as those employing fiber bragg gratings. It would be particularly advantageous if the method of improvement remained effective at higher temperatures, in order to avoid the low temperature limitations associated with alternate methodologies. It would be further advantageous if the increased response of the metal oxide material could be brought about by relatively well understood processes, such as doping, and demonstrated reversibility under high temperature conditions of interest.

Presented here is a method of detecting changes in the chemical composition of a gaseous stream by utilizing the optical response of doped oxide material having a relatively high carrier concentration. The optical response of the doped oxide materials disclosed are believed to stem predominantly from alterations to the carrier concentration that occur within changing gas atmospheres at elevated temperatures. By suitable selection of dopants in conjunction with high temperature stable metal oxides, the surprisingly effective method utilized within this disclosure provides a means whereby doped metal oxides having relatively high carrier concentrations are employed to generate improved signals under gaseous atmospheres which experience varying concentrations of reducing and oxidizing agents.

These and other objects, aspects, and advantages of the present disclosure will become better understood with reference to the accompanying description and claims.

SUMMARY

The disclosure provides a method of detecting a change in a chemical composition of a gas stream through the generally described steps of: (i) placing a doped oxide material comprising a doped metal oxide in the gas stream, we gas stream, where gas stream is at a temperature of at least 100° C.; (ii) contacting the doped oxide material with a monitored stream comprising some portion of the gas stream; (iii) illuminating the doped oxide material with incident light; (iv) collecting exiting light transmitted, reflected, scattered, or a combination thereof by the doped oxide material; (v) monitoring an optical signal based on a comparison of the incident light and the exiting light using optical spectroscopy, and (vi) detecting a shift in the optical signal, thereby detecting the change in the chemical composition.

The doped metal oxide has an empirical formula $M_aO_b$ where M is at least a first element and O is an oxygen anion, and where the doped metal oxide has a carrier concentration of at least $10^{18}/cm^3$, a bandgap of at least 2 eV, and an electronic conductivity of at least $10^1$ S/cm. In an embodiment, M is at least a first element and a second element and the doped metal oxide has the empirical formula $A_yB_xO_z$. In a further embodiment, the first element, the second element, and the oxygen anion form a recognized crystalline structure with a lattice system, and M and the oxygen anion are located at one of the special positions of the crystalline lattice. Exemplary doped metal oxides include but are not limited to AZO $(Zn_{1-x}Al_xO)$, ITO $(In_{2-x}Sn_xO_3)$, F-doped $SnO_2$, and Nb-doped TiO $(Ti_{1-x}Nb_xO_2)$. In another embodiment, the doped metal oxide is a non-stoichiometric metal oxide such as $In_2O_{3-x}$ in which the dopant can be considered to be a vacancy on the oxygen sublattice, or some other defect that is responsible for the non-stoichiometry.

The optical response of the doped oxide materials results from the high carrier concentration of the doped metal oxide, and the resulting impact of changing gas atmospheres on that relatively high carrier concentration. These changes in effective carrier densities of conducting metal oxide nanoparticles are postulated to be the predominant mechanism responsible for the change in measured optical absorption associated with free carriers. This surprising discovery is utilized to provide a means whereby doped metal oxides having relatively high carrier concentrations can be employed to generate useful signals indicating alterations in a surrounding gas atmosphere, based on resulting shifts in the optical signal.

The optical response of the doped oxide material is demonstrated to be relatively temperature dependent and generally applies for temperatures of at least 100° C. In an embodiment, the monitored stream has a temperature of at least 200° C. In a further embodiment, the monitored stream has a temperature of at least 200° C., and the change in the chemical composition is indicated by an increase or decrease in a signal-averaged optical signal of at least 0.1%. The optical response of the doped oxide material is additionally demonstrated to be monotonic relative to the concentration of a reducing or oxidizing gas. In an embodiment, the doped oxide material is utilized in a method for monitoring the concentration of a chemical species.

Measured optical responses of doped oxide materials have been observed to be significantly impacted by the degree of light scattering by the material. Light scattering is well known to be related to the degree of surface or interface roughness in the case of fairly dense and continuous thin films and particle size in the case of nanoparticle based films. In addition, the amount of light scattering is dependent upon the wavelength of interrogation and the optical constants of the doped oxide material. In particular, surface roughnesses of continuous films greater than approximately 5 nm, 10 nm, or 50 nm can cause a significant degree of light scattering in the UV, visible, and near-IR wavelength ranges with increasing surface roughnesses causing increased light scattering. Similarly, particle sizes of nanoparticle based films greater than approximately 10 nm, 20 nm, or 50 nm in diameter can also cause a significant degree of light scattering in the UV, visible, and near-IR wavelength ranges. In general, increasing surface roughnesses tend to cause increased light scattering at a given wavelength. In some cases it has been experimentally observed and theoretically shown that enhanced scattering can result in larger optical signal shifts and even change the sign of the shift over certain wavelength ranges as compared to relatively smooth films comprising doped metal oxides that do not exhibit measurable light scattering. This observation is typically attributed to an enhanced dependence of the optical signal on the real part of the dielectric constant of the doped metal oxide.

The novel process and principles of operation are further discussed in the following description.

BRIEF DESCRIPTION OF THE DRAWINGS

FIG. 2 illustrates a change in the optical absorbance of a doped metal oxide in response to changes to a chemical composition over a first wavelength range.

FIG. 3 illustrates a change in the optical absorbance of a doped metal oxide in response to changes to a chemical composition over a second wavelength range.

DETAILED DESCRIPTION

Figure 1:
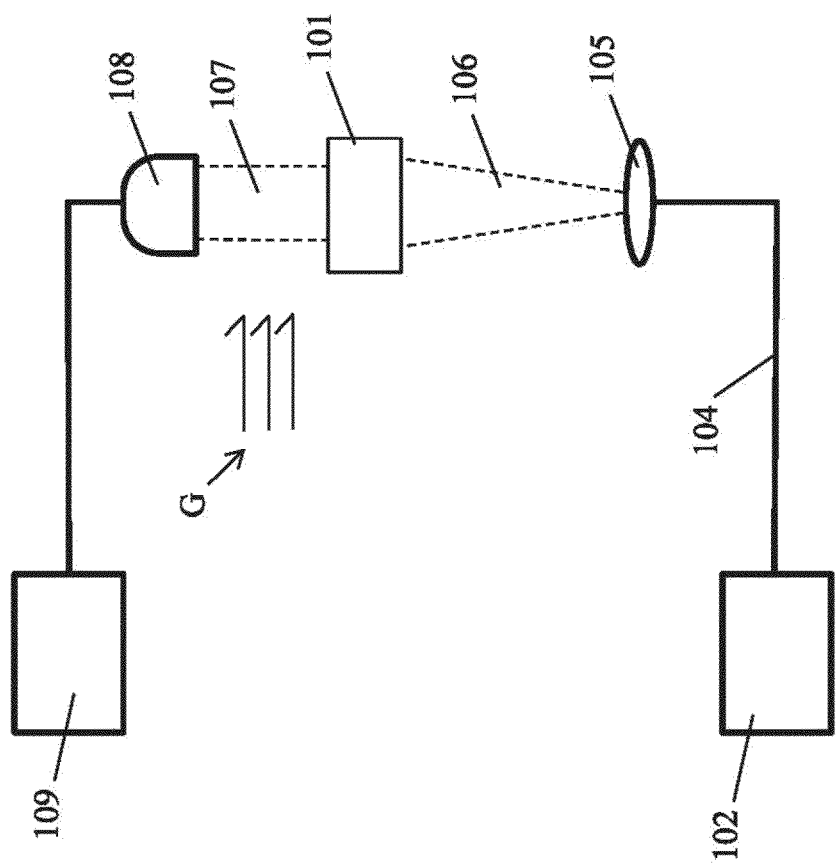
FIG. 1 illustrates a methodology for sensing changes to a chemical composition in a high temperature gas stream using the doped oxide material.

The following description is provided to enable any person skilled in the art to use the invention and sets forth the best mode contemplated by the inventor for carrying out the invention. Various modifications, however, will remain readily apparent to those skilled in the art, since the principles of the present invention are defined herein specifically to provide a method for detecting a change in the chemical composition of a gas stream using the optical response of a doped oxide material.

The disclosure provides a method for sensing changes to a chemical composition of a gas stream by utilizing a shift in the optical signal generated by a doped oxide material having a relatively high carrier concentration. This disclosure utilizes the surprising impact of carrier concentration increases on the optical signals generated, and specifies a manner in which the optical signal of the doped oxide material may serve as an indication of changing gas atmospheres. The impact of alterations to the carrier concentration of a material on resulting optical signals generated within a gaseous atmosphere is a surprising recognition. See Ohodnicki et al., "Plasmonic Transparent Conducting Metal Oxide Nanoparticles and Nanoparticle Films for Optical Sensing Applications," *Thin Solid Films* (2013), doi: 10.1016/j.tsf.2013.04.145. This disclosure provides a method by which this surprising effect may be utilized in order to measurably detect alterations in a surrounding gas atmosphere, by utilizing doped metal oxides with sufficiently high carrier concentrations such that the altered optical signal is measurably impacted.

The doped oxide material comprises a doped metal oxide, where the doped metal oxide has a carrier concentration of at least $10^{18}/cm^3$, a bandgap of at least 2 eV, and an electronic conductivity of at least $10^1$ S/cm, where the parameters are measured at a temperature of 25° C. The carrier concentration of the doped metal oxide is preferably at least $10^{19}/cm^3$, and the electronic conductivity is preferably at least $10^2$ S/cm, more preferably at least $10^3$ S/cm. The doped metal oxide is a compound having the empirical formula $M_aO_b$ where M is at least a first element and O is an oxygen anion. The doped metal oxide thus has the general properties associated with that group of materials known generically as transparent conducting oxides. In an embodiment, M is at least a first element and a second element and the doped metal oxide has the empirical formula $A_yB_xO_z$, where A is the first element, B is the second element, and O is an oxygen anion. In a further embodiment, the doped metal oxide has the empirical formula $A_{(1-x)}B_xO_z$. Exemplary doped metal oxides include but are not limited to AZO ($Zn_{1-x}Al_xO$), ITO ($In_{2-x}Sn_xO_3$) Nb-doped $TiO_2$ ($Ti_{1-x}Nb_xO_2$), and F-doped $SnO_2$. In an additional embodiment, the first element is a metal within groups 2-15 and the second element is a metal within groups 3-14. In another embodiment, the second element is F or Cl. In a further embodiment, the first element, the second element, and the oxygen anion form a crystalline structure having a lattice system such as cubic, hexagonal, tetragonal, rhombohedral, orthorhombic, monoclinic, or triclinic, and M and the oxygen anion are located at special positions within the lattice. See e.g., J. N. Lalena et al., *Principles of inorganic Material Design* (2nd Ed., 2010). In another embodiment, the second element is a cation or an anion within the crystalline structure of the doped metal oxide. In a further embodiment, the second element comprises less than 15 weight percent (wt. %) of the doped metal oxide.

In another embodiment, the doped metal oxide is a non-stoichiometric metal oxide having a carrier concentration of at least $10^{18}/cm^3$, a bandgap of at least 2 eV, and an electronic conductivity of at least $10^1$ S/cm, where parameters are specified at a temperature of 25° C. The carrier concentration of the non-stoichiometric metal oxide is preferably at least $10^{19}/cm^3$, and the electronic conductivity is preferably at least $10^2$ S/cm, more preferably at least $10^3$ S/cm. The non stoichiometric oxide may be, for example, of anion vacancy type, cation vacancy type, anion interstitial type, or cation interstitial type, as those terms are used in the art. See e.g., R. Xu et al., *Modern Inorganic Synthetic Chemistry* (2011), among others. Here, "non-stoichiometric oxide" means a metal oxide having the elemental composition $M_aO_b$ where M is at least a first element and O is an oxygen anion, and M and O are not combined in a definite proportion. In an embodiment, the non-stoichiometric oxide has an elemental composition $M_cO_{(d-z)}$, where M is at least the first element, O is the oxygen anion, c and d are natural numbers, and x is greater than 0.001, preferably greater than 0.01.

As indicated, the method disclosed is based in part on the recognition that alterations to the carrier concentration of a material impact the resulting optical signals generated, and that doped metal oxides with sufficiently high carrier concentrations are particularly effective for the measurable detection of alterations in a surrounding gas atmosphere. Correspondingly, doped metal oxides suitable for the method disclosed are described in terms of the physical parameters possessed by the doped metal oxide, such as a carrier concentration of at least $10^{18}/cm^3$, a bandgap of at least 2 eV, and an electronic conductivity of at least $10^1$ S/cm. As is understood in the art, for a given metal oxide, these physical parameters may be manipulated by carious physical processes, such as annealing treatments, certain manners of deposition, and other means. See e.g Chen et al., "Influence of Hydrogen on Al-doped ZnO Thin Films in the Process of Deposition and Annealing," *Transactions of Electrical and Electronic Materials* 10(3) (2009); see also Ota et al., "Fabrication of indium-tin-oxide films by dip coating process using ethanol solution of chlorides and surfactants," *Thin Solid Films* 411 (2002); see also Shigeno et al., "Formation of indium-tin-oxide films by dip coating process using indium dipropionate monohydroxide," *Thin Solid Films* 411 (2002), among others. Correspondingly, when this disclosure describes a doped metal oxide, where the doped metal oxide has a carrier concentration of at least $10^{18}/cm^3$, a bandgap of at least 2 eV, and an electronic conductivity of at least $10^1$ S/cm at 25° C., this is not intended to limit the doped metal oxide to those materials which display those parameters under all conditions and following all treatments. Rather, the method disclosed herein is intended to apply specifically when a doped metal oxide meets those conditions, regardless of whether those parameters can be manipulated by other processes existing outside this disclosure.

In a particular embodiment, the doped metal oxide has a carrier concentration of at least $10^{18}/cm^3$, a bandgap of at least 2 eV, and an electronic conductivity of at least $10^1$ S/cm at 25° C., and the doped metal oxide comprises a base oxide and a dopant, where the base oxide is one of $SnO_2$, ZnO, $In_2O_3$, $TiO_2$, $CeO_2$, $CO_3O_4$, $Fe_2O_3$, $CdO_2$, $Ta_2O_5$, $WO_3$, $Y_2O_3$, $ZrO_2$, $La_2O_3$, $SrTiO_3$, CaO, $Al_2O_3$, $SiO_2$, $LaSrO_3$, $IrO_2$, $MoO_3$, $Ga_2O_3$, or $Sb_2O_3$, and where the dopant is at least one of Al, In, Sn, Zn, Ti, Ce, Sc, Ga, Nb, Sb, Ta, Ni, Co, Fe, Mn, Si, P, F, and B.

In an embodiment, the doped metal oxide has a carrier concentration of at least $10^{18}/cm^3$, a bandgap of at least 2 eV, and an electronic conductivity of at least $10^1$ S/cm, where parameters are specified at a temperature of 25° C. following an elevated temperature reducing treatment. Here, "elevated temperature reducing treatment" means a treatment whereby the doped oxide material is contacted with a gaseous mixture having a composition of 4 vol. % $H_2$/balance $N_2$, where the gaseous mixture is at a temperature of at least 100° C., and where the contact occurs for a period of at least one hour. Such elevated reducing temperature treatments are generally effective for n-type doped metal oxides. Alternatively, in an embodiment, the doped metal oxide is a p-type doped metal oxide, and the parameters are specified at a temperature of 25° C. following an elevated temperature oxidizing treatment. Here, "elevated temperature oxidizing treatment" means a treatment whereby the doped oxide material is contacted with a gaseous mixture having a composition of 20 vol. % $O_2$/balance $N_2$, where the gaseous mixture is at a temperature of at least 100° C., and where the contact occurs for a period of at least one hour. The respective elevated temperature treatments may occur during the fabrication of the doped oxide material or as a post-fabrication annealing process. In these embodiments, the phrases "following an elevated temperature reducing treatment" and "following an elevated temperature oxidizing treatment" is not intended to imply that the specific temperature treatments themselves are required as a limitation within the method of this disclosure. Rather, the phrases are utilized herein merely as a specific means by which the doped oxide materials of this disclosure may be identified.

The doped oxide material may be utilized for sensing the change in the chemical composition of the gas stream at temperatures greater than about 100° C. based on the impact of the chemical composition on the free carrier concentration of the doped oxide material. Changes to the free carrier concentration directly impact the optical properties of the doped oxide material, which may be ascertained by monitoring optical transmission, reflection, scattering, and absorption spectra of the doped oxide material as ambient gas atmospheres are altered.

The basic principles of the method are illustrated at FIG. 1. At FIG. 1, light from light source 102 is directed along an optical fiber 104 and focused by lens 105 producing incident light 106 illuminating doped oxide material 101. Concurrently, exiting light 107 is collected behind the specimen using a probe 108 connected to a spectrophotometer 109. Data generated by spectrophotometer 109 or supporting equipment is processed, and an optical signal is displayed. The optical signal is a comparison of the incident light and the exiting light and indicates the absorption, transmission, reflection, and scattering of the incident light at certain wavelengths by doped oxide material 101.

Doped oxide material 101 is additionally in contact with a monitored stream G. Monitored stream G is at a temperature greater than 100° C. and comprised of a chemical composition of gaseous constituents with concentrations that may vary over time. In an embodiment, monitored stream G is periodically comprised of reducing species such as $H_2$, CO, $NH_3$, hydrocarbons, or mixtures thereof. As discussed, doped oxide material 101 comprises a doped metal oxide having a carrier concentration of at least $10^{18}/cm^3$, a bandgap of at least 2 eV, and an electronic conductivity of at least $10^1$ S/cm, where parameters are specified at a temperature of 25° C. In an embodiment, the doped oxide material is a doped oxide such as aluminum-doped zinc oxide (AZO), indium tin oxide (ITO), Nb-doped $TiO_2$ and others.

Incident light 106, exiting light 107, and doped oxide material 101 generate an optical signal which depends on the chemical composition of monitored stream G, and shifts in the optical signal at monitored wavelengths are indicative of a change in the chemical composition. As an example, FIG. 2 represents exemplary optical signals expected for a doped oxide material comprising AZO when the AZO doped oxide material is illuminated by incident light and exposed to a monitored stream. As indicated, the particular optical signals at FIG. 2 represent an absorbance over a band of wavelengths. Optical signal 210 is expected when the monitored stream contacting the doped oxide material is comprised of air with a substantial absence of $H_2$. In contrast, when the chemical composition of the monitored stream changes, such that the monitored stream comprises about 4% $H_2$, remainder $N_2$, the optical signal is expected to alter to optical signal 211, exhibiting a pronounced shift within the range of about 350 nm to about 550 nm, as illustrated. Similarly, FIG. 3 illustrates the optical signals 210 and 211 over a wider wavelength range as optical signal 310 and optical signal 311 respectively. Comparison of optical signals 310 and 311 clearly indicate a shift in the optical characteristic at longer wavelengths for the AZO gas sensing oxide when the monitored stream is altered from air to a composition of 4% $H_2$, remainder $N_2$.

As FIGS. 2 and 3 indicate, monitoring the optical signal over one or more wavelengths when the doped oxide material in is contact with a monitored stream provides a means by which the chemical composition of the monitored stream may be evaluated. The optical signal may be monitored directly through broadband wavelength interrogation and appropriate fitting procedures, or through indirect measurements by monitoring film transmittance, reflectance, scattering, or absorptance at one or more selected wavelength(s). For example, at FIG. 3, a shift in the optical signal may be detected by monitoring at the specific wavelength $\lambda_1$, and interpreting an increase in the absorption measured such as $\Delta_1$ as indicative of a shift from optical signal 310 to optical signal 311. In an embodiment, the shift in the optical signal is an increase or decrease in a signal-averaged transmittance, reflectance, absorptance, or scattering at a selected wavelength of at least 0.1%.

The disclosure thus provides a method of detecting a change in a chemical composition of a gas stream through the generally described steps of: (i) placing a doped oxide material comprising a doped metal oxide in the gas stream, where the gas stream is at a temperature of at least 100° C., where the doped oxide material comprises a doped metal oxide having a carrier concentration of at least $10^{18}/cm^3$, a bandgap of at least 2 eV, and an electronic conductivity of at least $10^1$ S/cm where parameters are specified at a temperature of 25° C. (ii) contacting the doped oxide material with a monitored stream comprising some portion of the gas stream; (iii) illuminating the doped oxide material with incident light; (iv) collecting exiting light transmitted, reflected, or a combination thereof by the doped oxide material; (v) monitoring an optical signal based on a comparison of the incident light and the exiting light using optical spectroscopy, and (vi) detecting a shift in the optical signal, thereby detecting the change in the chemical composition.

As discussed, the doped metal oxide has an empirical formula $M_aO_b$, where M is at least a first element and O is an oxygen anion. Exemplary doped metal oxides include but are not limited to AZO ($Zn_{1-x}Al_xO$), ITO ($In_{2-x}Sn_xO_3$), Nb-doped $TiO_2$ ($Ti_{1-x}Nb_xO_2$), and F-doped $SnO_2$. In an embodiment where M is a first element and a second element, the second element comprises less than 15 wt. % of the doped metal oxide.

The doped metal oxide may comprise the doped oxide material in conjunction with a combination of other materials, however the primary response observed, monitored, and discussed herein is the response of the doped metal oxide to the change in the chemical composition of the monitored stream. In an embodiment, the doped oxide material is a mixture of compounds, and the doped metal oxide comprises at least 25 wt. % and preferably 50 wt. % of the doped oxide material. In another embodiment, the doped oxide material is characterized by less than 1 wt. %, less than 0.1 wt. %, or undetectable noble metal deposits. Here a "noble metal deposit" means a deposit in contact with the doped oxide material where one or more noble metals comprise at least 90 wt. % of the noble metal deposit, and where the noble metal deposit is not a cation or anion of the $M_aO_b$ doped metal oxide and are not located at a special position of the $M_aO_b$ lattice structure. Noble metals within this context include gold, silver, platinum, palladium, ruthenium, rhodium, osmium, and iridium. In a further embodiment, the doped oxide material comprises less than 1 wt. %, less than 0.1 wt. %, or undetectable gold, silver, or palladium.

Within this disclosure, "optical signal" means a comparison of light incident on the doped oxide material and light exiting the doped oxide material at one or more wavelengths using optical spectroscopy. The optical signal may be expressed as, for example, a transmittance at the one or more wavelengths, an absorption at the one or more wavelengths, or any other parameters which indicate the absorption, transmission, reflection, scattering or other optical impacts on the incident light as a result of interaction with the doped oxide material. As is understood, optical spectroscopy based on a comparison of the incident light and the exiting light may indicate the absorption, transmission, reflection, scattering, and optical impacts which occur as a result of interaction between the incident light and the doped oxide material. See e.g., Ingle, James D., and Stanley R. Crouch, *Spectrochemical analysis*, Englewood Cliffs, N.J.: Prentice Hall, 1988; see also Sole, Jose, *An Introduction to the Optical Spectroscopy of Inorganic Solids* (2005); see also Sarid, Dror and Challener, William, *Modern introduction to Surface Plasmons: Theory, Mathematica Modeling, and Applications* (2010), among others.

Within this disclosure, a "shift in the optical signal" means a variation between a first optical signal and a second optical signal at one or more wavelengths, where the first optical signal is generated at a first time and the second optical signal is generated at a second time, and where both the first optical signal and the second optical signal are generated by illuminating the doped oxide material with the light source emitting the incident light, collecting the exiting light, and comparing the incident light and the exiting light using optical spectroscopy. The shift in the optical signal may be recognized by detecting a variation between optical signals at any monitored wavelength or by variations at multiple wavelengths over a band of wavelengths. For example, the variation may be detected by monitoring a transmittance at a specific wavelength, the specific wavelength of an optical signal edge within a specified wavelength range, the wavelength of an optical signal local maxima, a variation in the optical signal breadth, a variation in the optical signal amplitude, a variation in the optical signal full width at half maximum (FWHM), or any other techniques which may serve to indicate a variation between the first optical signal and a second optical signal, in an embodiment, the shift in the optical signal means a variation of at least 0.1% between a first time-averaged optical signal and a second time-averaged optical signal in either transmittance, absorption, or reflectance at a specific wavelength.

The shift in the optical signal as disclosed here is generally not constrained to a specific wavelength or band of wavelengths. As discussed, the shift in optical signal may be a shift at one specific wavelength, or may be a shift over a monitored band of wavelengths. For example, the shift may occur at one or more wavelengths typically considered to be ultraviolet, visible, or infrared as those terms are used in the art.

Without being bound by theory, the optical response of the doped oxide materials achieved within this disclosure is believed to result from the high carrier concentration of the metal oxide comprising the doped oxide material, and a resulting impact on that relatively high carrier concentration by changing gas atmospheres. It is known that certain metal oxides such as $TiO_2$, ZnO, and $SnO_2$ exhibit changes in electrical resistance as a function of temperature and/or in response to changing gas atmospheres, which is usually associated with a change in the free carrier density of the oxide. Additionally, for conducting metal oxides such as AZO, a strong dependence of electrical resistance and carrier concentration on ambient atmospheric conditions at high temperatures is also expected. See e.g., Sagar et al. "influence of hydrogen incorporation in sol-gel derived aluminum doped ZnO thin films," *Thin Solid Films* (2005); and see Pearton et al., "Recent progress in processing and properties of ZnO," *Progress in Materials Science* (2005). Within this disclosure, these changes in effective carrier densities of conducting metal oxide nanoparticles in response to changing ambient gas atmospheres are postulated to be responsible for the change in measured optical absorption associated with free carriers. This surprising discovery is utilized within this disclosure to provide a means whereby doped metal oxides having relatively high carrier concentrations can be employed to generate useful signals indicating alterations in a surrounding gas atmosphere, based on resulting shifts in the optical signal.

Figure 4:
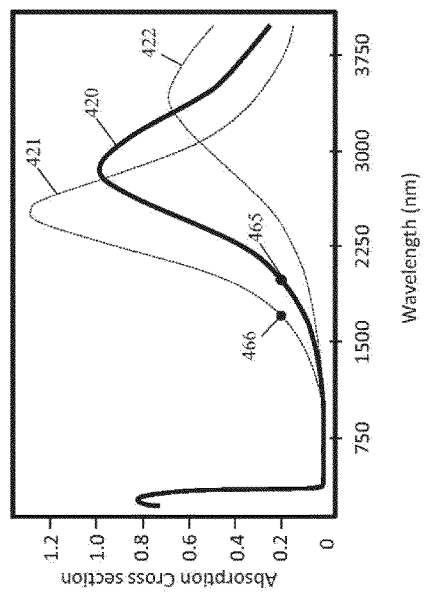
FIG. 4 illustrates a simulated change in the optical absorbance of a doped metal oxide in response to changes in the carrier concentration when the doped oxide consists of isolated nanoparticles roughly 5 nm in diameter.

As an example of the impact of carrier concentration on the optical signal, simulated effects of changing a carrier concentration N on the measured optical absorption of AZO nanoparticles are illustrated at FIG. 4. Similar results are presented at FIG. 5 for a continuous and dense 200 nm thin film of AZO. The impact of a change in the carrier concentration N on the absorption cross-section was approximated by modifying empirical optical constants as follows: (1) the effective carrier concentration N was increased or decreased by 30% from a nominal value and (2) the bandgap parameter employed in the interband electronic transitions dielectric function was allowed to vary according to the well-known Burstein-Moss shift. At FIG. 4, a nominal carrier concentration N, a 30% increase in the carrier concentration N, and a 30% decrease in the carrier concentration N is illustrated as curve 420, curve 421, and curve 422 respectively. At FIG. 5, a nominal carrier concentration N, a 30% increase in the carrier concentration N, and a 30% decrease in the carrier concentration N is illustrated as curve 520, curve 521, and curve 522 respectively. The simulated results clearly illustrate a shift of the LSPR absorption peak (nanoparticles) or the onset of free carrier absorption (dense thin films) to shorter wavelengths with an increase in the carrier concentration N. The assumed shift also results in the prediction of a measurable change in optical absorptance in the vicinity of the band-edge due to the Burstein-Moss effect. See Ohodnicki et al., *Thin Solid Films* (2013).

Figure 7:
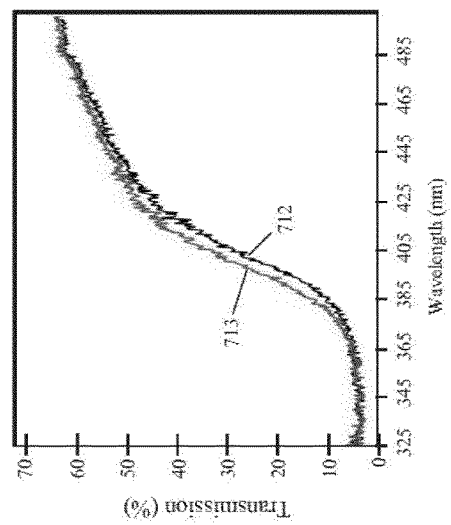
FIG. 7 illustrates a change in the optical transmission of a doped metal oxide in response to changes to a chemical composition over a second wavelength range.
Figure 6:
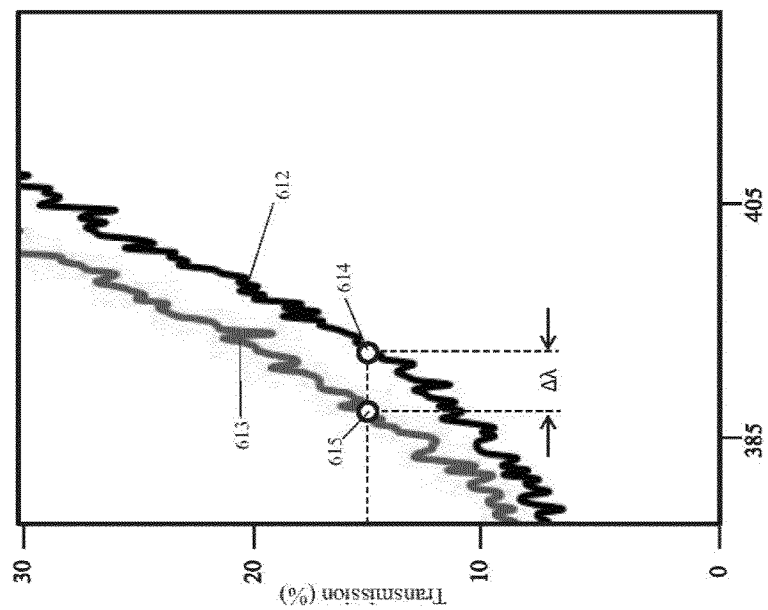
FIG. 6 illustrates a change in the optical transmission of a doped metal oxide in response to changes to a chemical composition over a first wavelength range.

As a further example, FIG. 6 represents optical signals 612 and 613 generated by a doped oxide material of AZO, where the AZO is a 1% Al:ZnO sol-gel film illuminated by incident light and exposed to monitored streams at a temperature of about 400° C. Optical signals 612 and 613 are illustrated over a wider wavelength range at FIG. 7 as optical signals 712 and 713 respectively. At FIG. 6, optical signal 612 illustrates transmission and represents the optical signal when the monitored stream consists of $N_2$. Similarly, optical signal 613 illustrates transmission and represents the optical signal when the monitored stream consists of a mixture of 4% $H_2$ with background $N_2$. As indicated, the optical signal of the AZO doped oxide material shifts on exposure to $H_2$ and indicates increased transmission compared to the previous environment of N2 for a fixed wavelength. Additionally, optical signal edges for the respective optical signals are illustrated generally as point 614 on optical signal 612 and point 615 on optical signal 613, where points 614 and 615 represent about a 15% transmission. As shown, exposure of the AZO doped oxide material to a reducing atmosphere of $H_2$ shifts the optical signal edge to a shorter wavelength. The shift of the optical signal edge from point 614 to point 615 is indicative of the shift in the optical signal of the AZO doped oxide material.

Correspondingly, in an embodiment, the exiting light collected after illumination of the doped oxide material with incident light has a optical signal edge between 250 and 600 nanometers, and the shift in the optical signal is represented by a shift in the band edge. In a further embodiment, the change in the chemical composition is an increased concentration of a reducing gas, and the shift in the optical signal edge is a shift to a lower wavelength.

Within this disclosure, a "optical signal edge" when specified as present within a described wave length range means a specific wavelength where a specified percentage of the incident light is transmitted through the doped oxide material. For example, points 614 and 615 at a specified percentage of about 15% within a wavelength range from about 385 nm to about 405 nm at FIG. 6. Similarly, a "shift in the optical signal edge" means a wavelength difference between a first wavelength and a second wavelength, where the specified percentage of the incident light is transmitted, absorbed, reflected, or scattered through the doped oxide material at both the first wavelength and the second wavelength. For example, at FIG. 6, a shift in the optical signal edge Δλ which occurs at the specified percentage of about 15% at FIG. 6. However, within this disclosure, an optical signal edge may be defined using any percentage as the specified percentage and any range as the described wave length range. For example at FIG. 4, an optical signal edge might be defined by points 465 and 466 at a specified percentage of 20% over a wavelength range from 750 nm to 2250 nm, and a shift in the optical signal edge from point 465 to point 466 might be similarly described. In an embodiment, the optical signal edge occurs over a wavelength range from 250 nm to 550 nm. In another embodiment, the optical signal edge occurs over a wavelength range from 1000 nm to 3750 nm.

Figure 8:
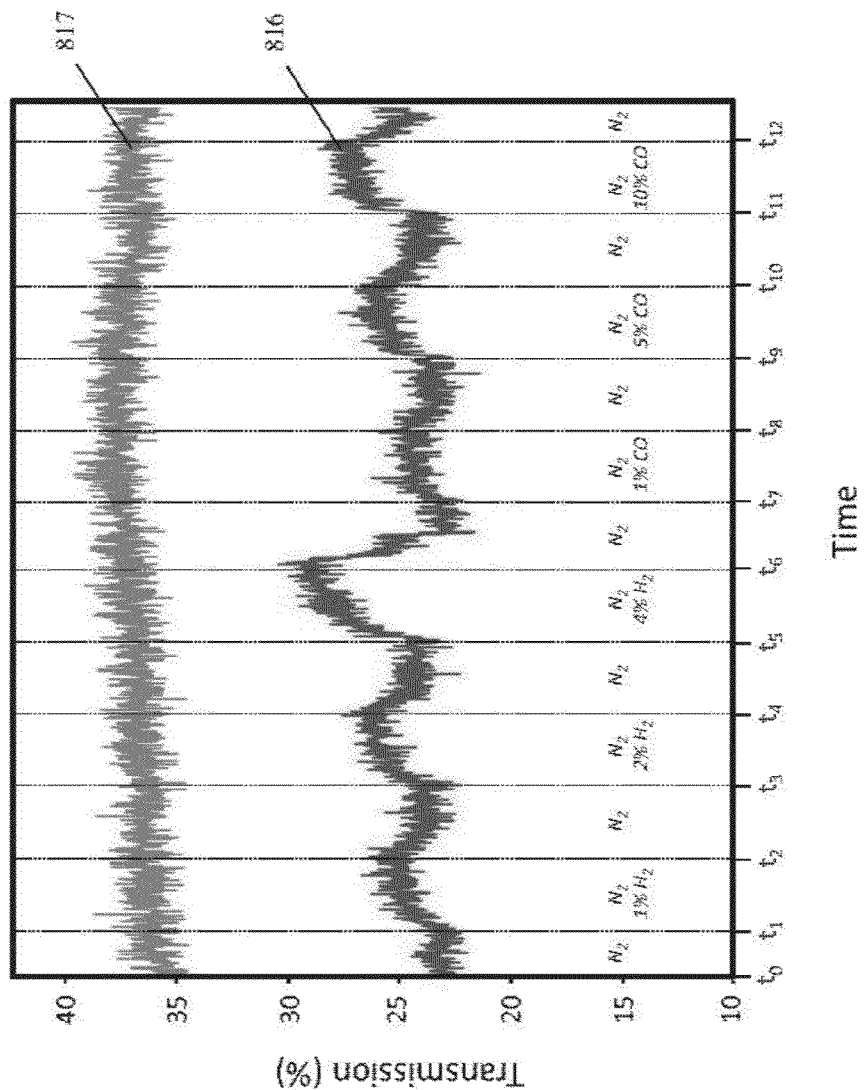
FIG. 8 illustrates a change in the optical transmission of a doped metal oxide in response to changes to a chemical composition at a specific wavelength for various temperatures.

FIG. 8 similarly illustrates the optical signal for a AZO doped oxide material illuminated by incident light and exposed to a monitored stream at a temperature of about 400° C., where the AZO is a 1% Al:ZnO sol-gel film, and where the monitored stream is a $N_2$ background with periodically increasing concentrations of CO and $H_2$. Optical signal 816 is indicated as a transmittance response versus time at a specific wavelength of 400 nm, with specific time points indicated as $t_i$ (i=0, 1, 2, ... 10). At FIG. 8, between generally times $t_1$ to $t_2$, $t_3$ to $t_4$, and $t_5$ to $t_6$, the AZO doped oxide material is exposed to 1 volume percent (vol. %) $H_2$, 2 vol. % $H_2$, and 4 vol. % $H_2$ respectively, all with background $N_2$. Between generally times $t_0$ to $t_1$, $t_2$ to $t_3$, and $t_4$ to $t_5$, the AZO doped oxide material is exposed to only the background $N_2$. As indicated by optical signal 816, exposure to the varying concentrations of $H_2$ generates a shift in the optical signal as indicated by an increase in the transmittance at the specific wavelength of 400 nm, and is consistent with a band edge shift toward reduced wavelengths within a wavelength range of, for example, from about 380-nm to about 420 nm. Similarly at FIG. 8, between generally times $t_7$ to $t_8$, $t_9$ to $t_{10}$, and $t_{11}$ to $t_{12}$, the AZO doped oxide material is exposed to 1 vol. % CO, 5 vol. % CO, and 10 vol. % CO respectively, all with background $N_2$, and generally between times $t_6$ to $t_7$, $t_8$ to $t_9$, $t_{10}$ to $t_{11}$, and greater than $t_{12}$, the AZO doped oxide material is exposed to only the background $N_2$. Exposure to the varying concentrations of CO additionally generates a shift in the optical signal as indicated by an increase in the transmittance at the wavelength of 400 nm, and is consistent with a band edge shift toward reduced wavelengths.

At FIG. 8, the elapsed time between given time points $t_i$ and $t_{i+1}$ are generally on the order of 30 minutes. As car be observed, the shift in the optical signal generated by the doped oxide material is generally a reversible phenomena, as noted by the return towards previous levels of transmission between times $t_0$ to $t_1$, $t_2$ to $t_3$, $t_4$ to $t_5$, $t_6$ to $t_7$, $t_8$ to $t_9$, $t_{10}$ to $t_{11}$, and greater than $t_{12}$, when the $H_2$ and CO are removed and the atmosphere is returned to $N_2$. This reversibility provides clear advantage in an instrument intended to sense changes in a chemical composition when concentrations are expected to vary periodically. Additionally, the optical signals display a monotonic behavior with magnitudes dependent on the specific concentration of the gaseous constituent present. In the case of $H_2$, this can be observed by comparison of the transmission levels between times $t_1$ to $t_2$, $t_3$ to $t_4$, and $t_5$ to $t_6$ when the atmosphere is 1 vol. %, $H_2$, 2 vol. % $H_2$, and 4 vol. % $H_2$ respectively, where the transmission levels are seen to increase with increasing concentrations of $H_2$. Similarly, in the case of CO, this is observed by comparison of the transmission levels between times $t_7$ to $t_8$, $t_9$ to $t_{10}$, and $t_{11}$ to $t_{12}$, when the atmosphere is 1 vol. % CO, 5 vol. % CO, and 10 vol. % CO respectively, and where the transmission levels are seen to increase with increasing concentrations of CO.

Further at FIG. 8, optical signal 817 is indicated as a transmittance response versus time at a wavelength of 400 nm under the same conditions as optical signal 816, except that the monitored stream is at a temperature of about 200° C. As illustrated by the comparison of optical signals 816 and 817, shifts in optical signal of the metal oxide sensing material in response to varying gas concentrations generally become more pronounced as temperature is increased, as will be discussed.

Figures 9, 10:
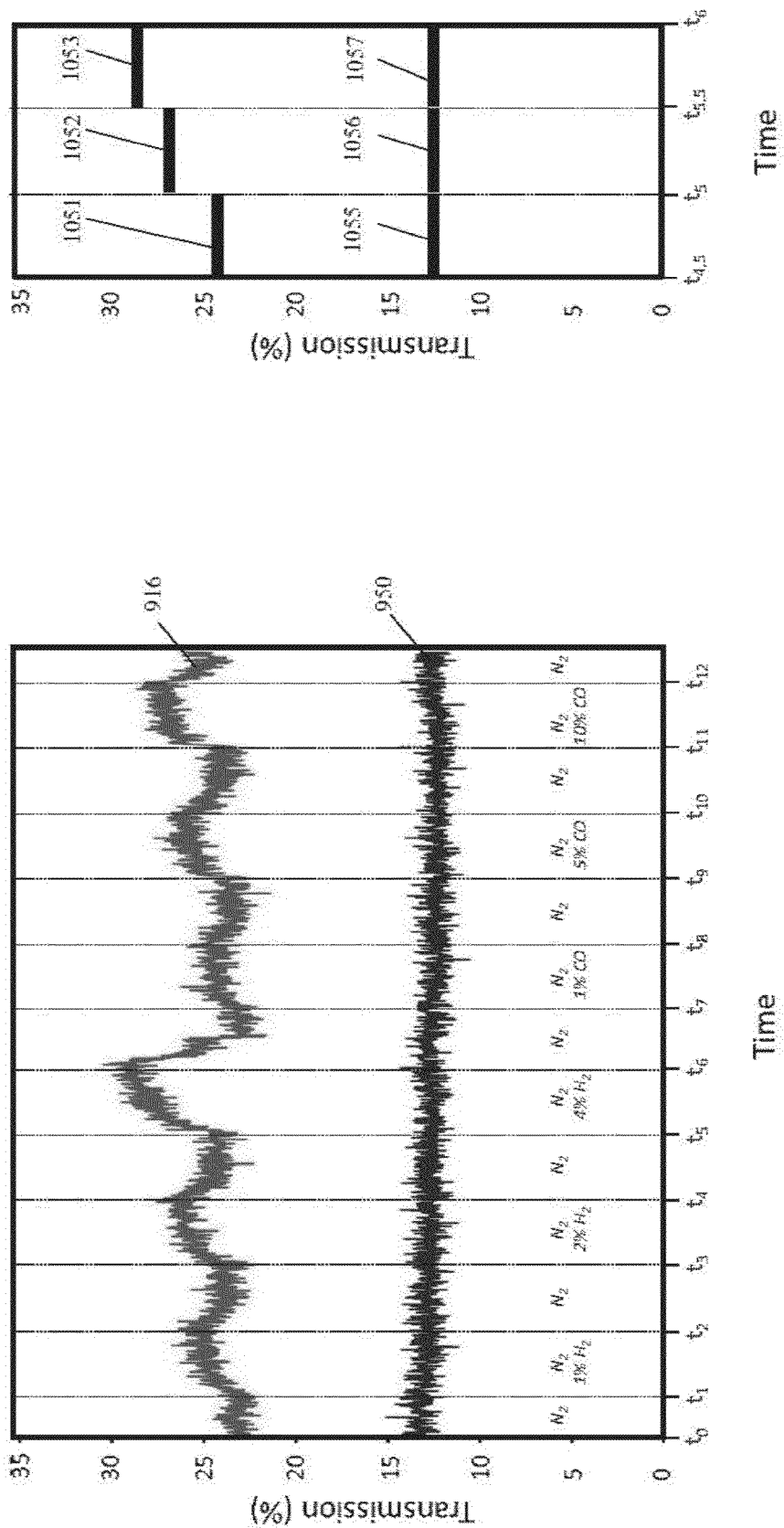
FIG. 9 illustrates a change in the optical transmission of a doped metal oxide in response to changes to a chemical composition compared to changes obtained in an undoped case at a fixed temperature.
FIG. 10 illustrates a change in the optical transmission of a doped metal oxide using a signal-averaged indication.

The impact of utilizing a doped oxide in order to increase the carrier concentration, and thereby increase or make measurable a shift in optical signal as gas atmospheres are altered at a temperature of 400° C., is demonstrated at FIG. 9. FIG. 9 reproduces optical signal 816 for the 1% Al:ZnO sol-gel film as optical signal 916 and similarly illustrates the monitored stream of $N_2$ background with periodically increasing concentrations of CO and $H_2$, as discussed and indicated for FIG. 8. FIG. 9 additionally illustrates the response in optical signal for an undoped film comprising zinc oxide (ZnO), shown as optical signal 950. As illustrated, under the same conditions, and in comparison to optical signal 916, the optical signal 950 generated by undoped ZnO provides no apparent response to the changes in the chemical composition. At FIG. 9, the increase in the carrier concentration afforded by providing a doped metal oxide as the gas sensing material allows the optical signal generated to be utilized as a gas sensing mechanism.

In an embodiment, the change in the chemical composition of the monitored stream is indicated by an increase or decrease in a signal-averaged optical signal of at least 0.1%, where the signal-averaged optical signal is generated through a signal processing technique applied in the time domain, and where the increase or decrease of 0.1% means that an observed signal-averaged optical signal is at least 0.1% greater or lesser than an initial signal-averaged optical signal. For example, an increase or decrease of 0.1% in an observed signal-averaged optical signal when the signal-averaged optical signal is a transmittance or absorptance characterized as $\tau_\lambda = I/I_o$ or $A_\lambda = (I_o - I)/O_o$ respectively, where $I_o$ is the intensity of the incident light and where I is the intensity of the exiting light at a wavelength $\lambda$, and where intensity refers to a power transmitted per unit area. In an embodiment, the signal-averaged optical signal is a time-averaged optical signal based on an absorption, transmission, scattering, or reflection generated using the doped oxide material and averaged over some time interval $\Delta t$. As an example, FIG. 10 represents time-averaged optical signals for the optical signals 916 and 950 of FIG. 9 at the wavelength $\lambda$ of 400 nm. FIG. 10 indicates the times $t_5$ and $t_6$ of FIG. 9, and additionally includes $t_{4.5}$ and $t_{5.5}$, where $t_{4.5}$ is a midpoint time between $t_4$ and $t_5$ of FIG. 9 and $t_{5.5}$ is midpoint time between $t_5$ and $t_6$ of FIG. 9. Time-averaged optical signals 1051, 1052, and 1053 represent optical signal 916 averaged over the time interval from $t_{4.5}$ to $t_5$, $t_5$ to $t_{5.5}$, and $t_{5.5}$ to $t_6$ respectively, and generally indicate shifts in time-averaged optical signals of at least a 0.1% change in transmission in response to the changing chemical compositions between times $t_{4.5}$ and $t_6$. Additionally illustrated for reference are time-averaged optical signals 1055, 1056, and 1057 representing optical signal 950 averaged over the time intervals $t_{4.5}$ to $t_5$, $t_5$ to $t_{5.5}$, and $t_{5.5}$ to $t_6$ respectively, and illustrating no apparent response in the time-averaged optical signal when the sensing material is an undoped ZnO, Techniques for the generation of signal-averaged optical signals are known in the art. See e.g. R. Lyons, *Understanding Digital Signal Processing* (3$^{rd}$ Ed., 2010); and see R. Northrup, *Analysis and Application of Analog Electronic Circuits to Biomedical Instrumentation* (2005), among others.

Figure 11:
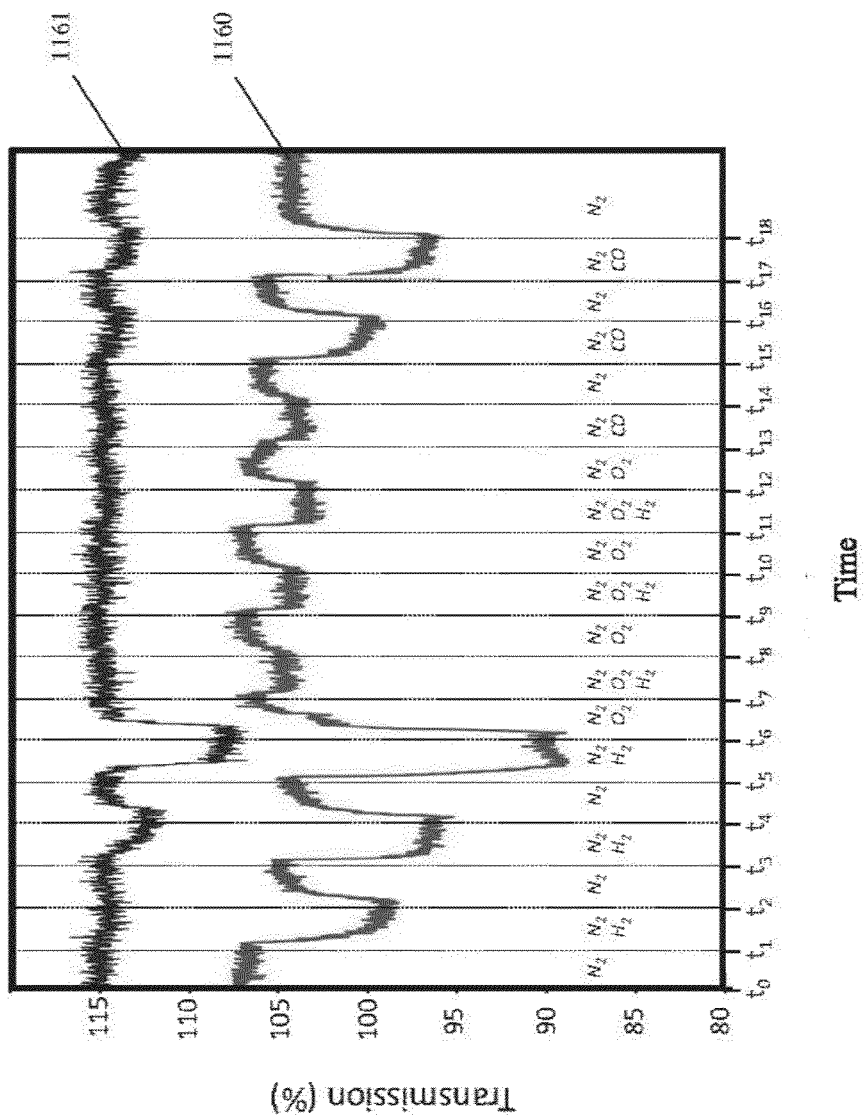
FIG. 11 illustrates a change in the optical transmission of a doped metal oxide in response to reducing and oxidizing gases.

FIG. 11 further illustrates the impact of utilizing a doped oxide in order to increase the carrier concentration and thereby increase the shift in an optical signal generated as gas atmospheres are altered. At FIG. 11, an optical signal at 2400 nm generated by a doped oxide material comprising 1% Al:ZnO deposited on a silica based optical fiber is illustrated as optical signal 1160. A correspondingly optical signal generated by undoped ZnO is illustrated as optical signal 1161. Transmissions referenced relative to measured values at room temperature in air. The 1% Al:ZnO and undoped ZnO was illuminated by incident light and exposed to a monitored stream at a temperature of about 400° C., where the monitored stream is a $N_2$ background with periodically increasing concentrations of $H_2$, CO, and $O_2$. Between generally times $t_1$ to $t_2$, $t_3$ to $t_4$, and $t_5$ to $t_6$, the doped oxide material was exposed to 1 vol. % $H_2$, 2 vol. % $H_2$, and 4 vol. % $H_2$ respectively, all with background $N_2$, while between $t_0$ to $t_1$, $t_2$ to $t_3$, and $t_4$ to $t_5$ the doped oxide material was exposed to $N_2$ only. Between generally times $t_7$ to $t_8$, $t_9$ to $t_{10}$, and $t_{11}$ to $t_{12}$, the doped oxide material was exposed to 1 vol. % $H_2$/5 vol. % $O_2$, 2 vol. % $H_2$/5 vol. % $O_2$, and 4 vol. % $H_2$/5 vol. % $O_2$ respectively against background $N_2$, while between $t_6$ to $t_7$, $t_8$ to $t_9$, $t_{10}$ to $t_{11}$, and $t_{11}$ to $t_{12}$ the doped oxide material was exposed to 5 vol. % $O_2$ with/background $N_2$. Between generally times $t_{13}$ to $t_{14}$, $t_{15}$ to $t_{16}$, and $t_{17}$ to $t_{18}$, the doped oxide material was exposed to 1 vol. % CO, 5 vol. % CO, and 10 vol. % CO respectively, all with background $N_2$, while between $t_{14}$ to $t_{15}$, $t_{16}$ to $t_{17}$, and greater than $t_{18}$ the doped oxide material was exposed to $N_2$ only. As indicated by FIG. 11 and a comparison of optical signals 1160 and 1161, the impact of doping to increase the carrier concentration significantly increases the response of the optical signal as gas atmospheres are altered. Note also the monotonic behavior of optical signal 1160, with magnitudes dependant on the specific concentration of the gaseous constituent present. The measurable response of undoped ZnO at this temperature is thought to be attributed to an increase in carrier concentration with temperature for the undoped oxide and could not be resolved for corresponding measurements performed with films deposited on planar substrates.

FIGS. 9 and 11 clearly indicate the advantage of utilizing a doped metal oxide in order to increase the carrier concentration and improve the optical signal response of oxide materials to changes in a surrounding gas atmosphere. In one sense, this disclosure provides a method of improving the optical signal response of a metal oxide having a carrier concentration less than $10^{18}/cm^3$ under the conditions described by doping the metal oxide, thereby generating a doped metal oxide having a carrier concentration of at least $10^{18}/cm^3$ under the conditions described, and thereby improving the optical response. This method of improvement exploits the discovered relationship between carrier concentrations and shifts in optical signal in response to surrounding gaseous atmospheres, as previously discussed and illustrated at FIGS. 4 and 5.

Figure 13:
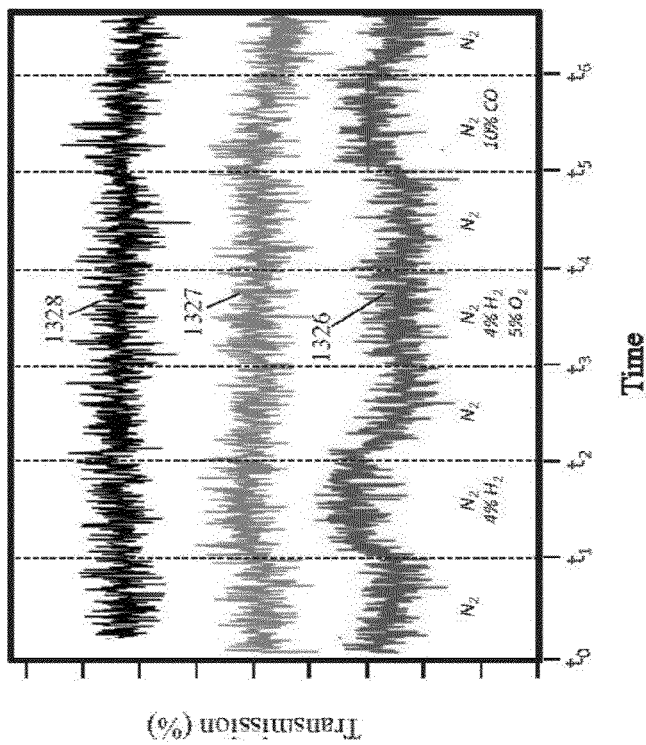
FIG. 13 illustrates a change in the optical transmission of a doped metal oxide in response to changes to a chemical composition at a second wavelength for various temperatures.
Figure 12:
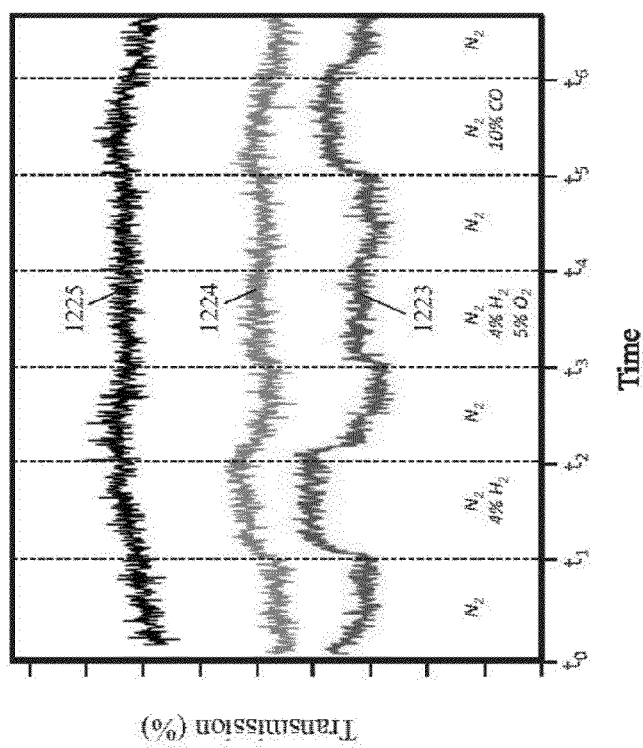
FIG. 12 illustrates a change in the optical transmission of a doped metal oxide in response to changes to a chemical composition at a first wavelength for various temperatures.
Figure 14:
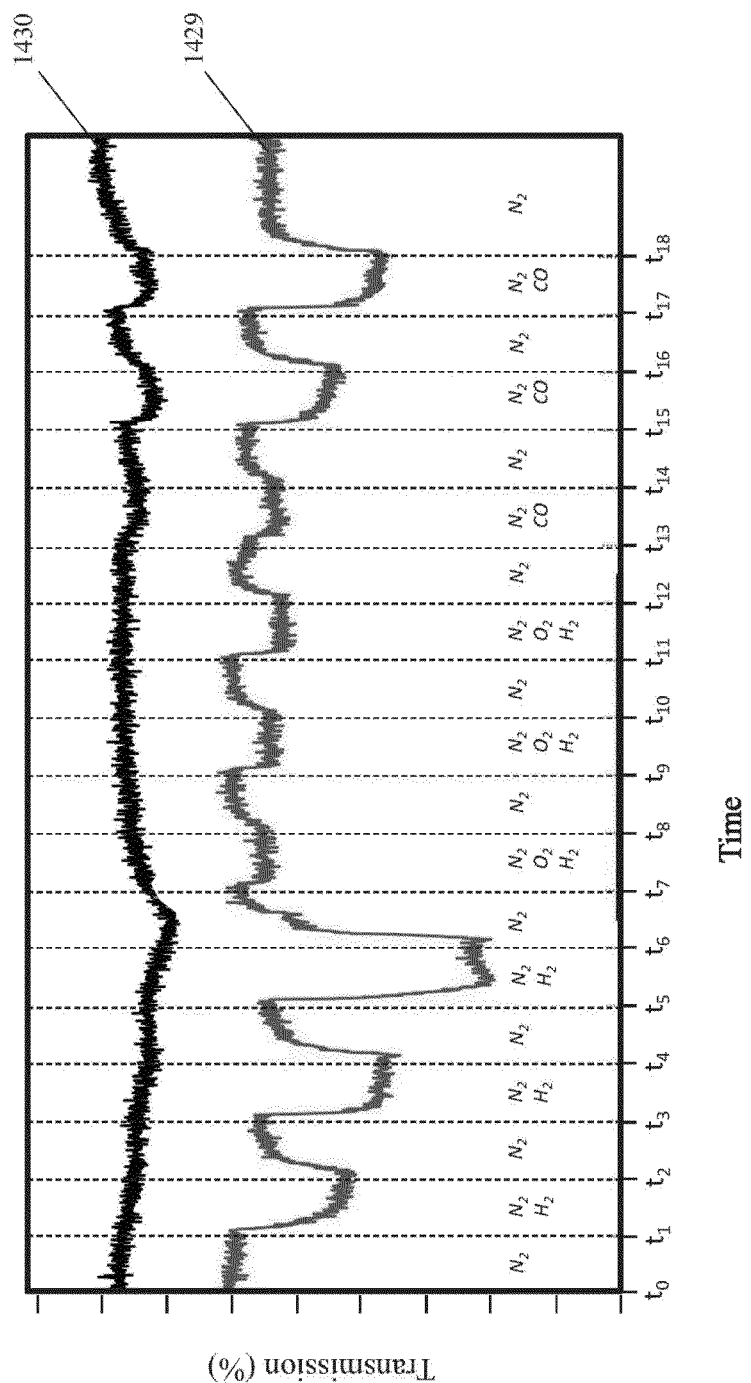
FIG. 14 illustrates a change in the optical transmission of a doped metal oxide in response to changes to a chemical composition at a third wavelength for various temperatures.

Additionally, as previously mentioned, shifts in optical signal of the metal oxide sensing material in response to varying gas concentrations generally become more pronounced as temperature is increased. The impact of temperature on the response of the doped oxide material is further illustrated at FIGS. 12, 13 and 14. FIGS. 12, 13, and 14 illustrate optical signals generated using a doped oxide material comprising 1% Al:ZnO, where the doped oxide material was coated on an optical fiber, as will be discussed. The AZO coated optical fiber was subjected to a series of gas concentrations at varying temperatures, and transmissions at 475 nm, 750 nm, and 2400 nm were monitored.

FIG. 12 illustrates transmission for the AZO coated optical fiber monitored at 475 nm. Optical signal 1223 corresponds to a temperature of 400° C., optical signal 1224 corresponds to a temperature of 300° C., and optical signal 1225 corresponds to a temperature of 200° C. The atmosphere between $t_0$ to $t_1$, $t_2$ to $t_3$, and $t_4$ to $t_5$ was $N^2$, while the atmosphere between $t_1$ to $t_2$ was 4 vol. % $H_2$/background $N_2$, between $t_3$ and $t_4$ was 4% $H_2$/5 vol. O2/background $N_2$, and between $t_5$ and $t_6$ was 10 vol. % CO background $N_2$. As indicated, there is an increase in the transmission for the 300° C. (optical signal 1224) and 400° C. (optical signal 1223) temperatures when the AZO coated optical fiber is exposed to a reducing gas. A measurable response is not clearly resolved for the 200° C. test (optical signal 1225). Additionally, no response was observed at room temperature. The mechanism for an increase in transmission in the band-edge region due to reducing gas exposure at elevated temperature is an increase in the free carrier concentration of the film.

Similarly, FIG. 13 illustrates transmission for the AZO coated optical fiber monitored at 750 nm. Optical signal 1326 corresponds to a temperature of 400° C., optical signal 1327 corresponds to a temperature of 300° C., and optical signal 1328 corresponds to a temperature of 200° C. The atmosphere between $t_0$ to $t_1$, $t_2$ to $t_3$, and $t_4$ to $t_5$ was $N_2$, while the atmosphere between $t_1$ to $t_2$ was 4 vol. % $H_2$/background $N_2$, between $t_3$ and $t_4$ was 4% $H_2$/5 vol. % O2/background $N_2$, and between $t_5$ and $t_6$ was 10 vol. % CO/background $N_2$. At FIG. 13, there is an increase in the transmission for the 300° C. (optical signal 1327) and 400° C. (optical signal 1326) temperatures when the AZO coated optical fiber is exposed to a reducing gas, but a measurable response is not clearly resolved for the 200° C. test (optical signal 1328), and additionally no response was observed at room temperature. Possibly, broadband transmission increase responses in the visible and near-IR range for AZO films on planar substrates and AZO coated fiber sensors can be attributed to changes in the real part of the dielectric constant of AZO over this wavelength range due to the change in free carrier density. As discussed previously, this effect can also be enhanced in some cases due to surface roughness which causes scattering of light.

FIG. 14 illustrates transmission for the AZO coated optical fiber monitored at 2400 nm. Optical signal 1429 corresponds to a temperature of 400° C., and optical signal 1430 corresponds to a temperature of 200° C. The atmosphere between $t_0$ to $t_1$, $t_2$ to $t_3$, $t_4$ to $t_5$, $t_6$ to $t_7$, $t_8$ to $t_9$, $t_{10}$ to $t_{11}$, $t_{12}$ to $t_{13}$, $t_{14}$ to $t_{15}$, and $t_{16}$ to $t_{17}$ was $N_2$. Between $t_1$ to $t_2$, $t_3$ to $t_4$, and $t_5$ to $t_6$ the atmosphere was 1 vol. % $H_2$, 2 vol. % $H_2$, and 4 vol. % $H_2$ respectively, all with a background of $N_2$. Between $t_7$ to $t_8$, $t_9$ to $t_{10}$, and $t_{11}$ to $t_{12}$ the atmosphere was 1 vol. % $H_2$/5 vol. % $O_2$, 2 vol. % $H_2$/5 vol. % $O_2$, and 4 vol. % $H_2$/5 vol. % $O_2$ respectively, all with a background of $N_2$. Between $t_{13}$ to $t_{14}$, $t_{15}$ to $t_{16}$, and $t_{17}$ to $t_{18}$ the atmosphere was 1 vol. % CO, 5 vol. % CO, and 10 vol. % CO respectively, all with a background of $N_2$. At FIG. 14, there is a decrease in the transmission for the 400° C. (optical signal 1429) temperature when the AZO coated optical fiber is exposed to a reducing gas, but a useful measurable response is not resolved for the 200° C. test due to the long time constants and weak dynamic response (optical signal 1430), and additionally no response was observed at room temperature. This decrease in transmission occurs due to free carrier absorption of the conducting oxide.

As a result of the temperature dependence discussed above and illustrated at FIGS. 8, 12, 13, and 14, when utilizing the doped oxide material to detect the changing chemical composition of a monitored stream based on shift in the optical signal, the disclosed method specifies a monitored stream temperature of at least 100° C. Additionally, in an embodiment, the monitored stream has a temperature of at least 200° C. In a further embodiment, the monitored stream has a temperature of at least 200° C. and the change in the chemical composition is indicated by an increase or decrease in a signal-averaged optical signal of at least 0.1%, where the signal-averaged optical signal is characterized as $\tau_\lambda = I/I_o$ or $A_\lambda = (I_o - I)/I_o$, as previously discussed. In a further embodiment, the monitored stream temperature is greater than 400° C., and the doped metal oxide is a doped metal oxide having a temperature programmed reduction temperature of at least 400° C.

Figure 5:
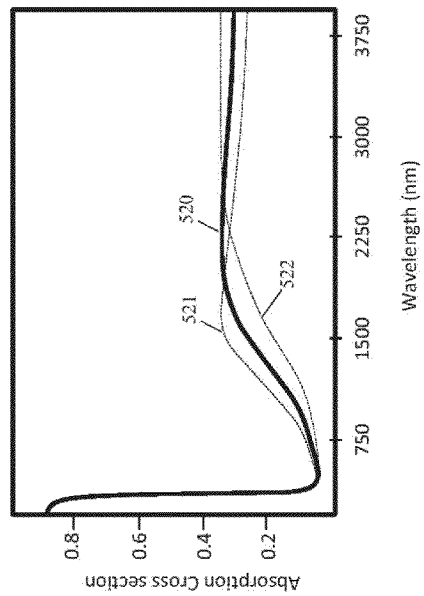
FIG. 5 illustrates a simulated change in the optical absorbance of a doped metal oxide in response to changes in response to changes in the carrier concentration when the doped oxide consists of a continuous, smooth thin film approximately 200 nm in thickness.
Figure 18:
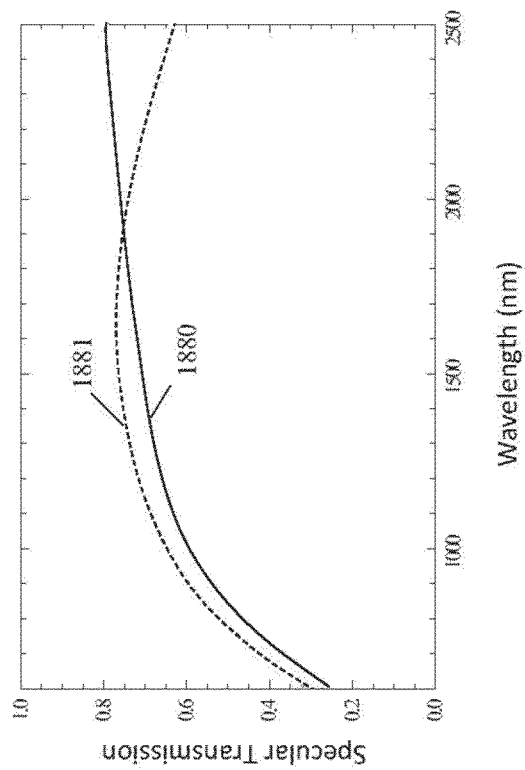
FIG. 18 illustrates a simulated transmittance spectrum for a doped metal oxide with a second surface roughness showing an enhanced broadband response due to scattering.
Figure 17:
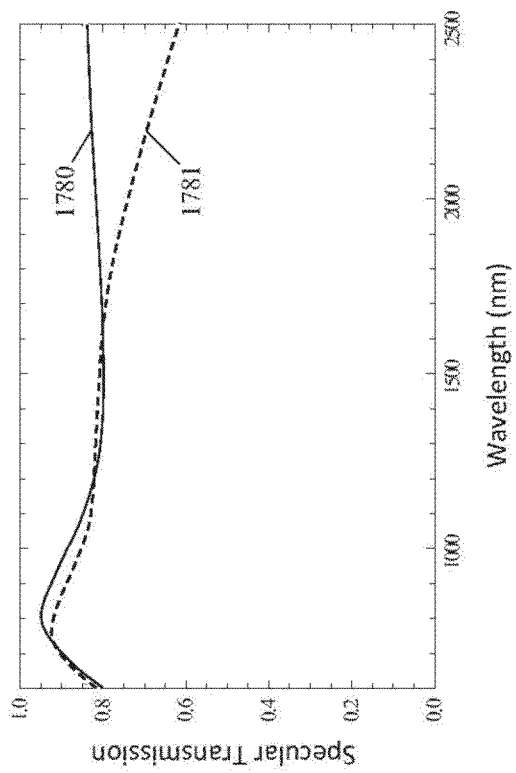
FIG. 17 illustrates a simulated transmittance spectrum for a doped metal oxide with a first surface roughness.
Figure 20:
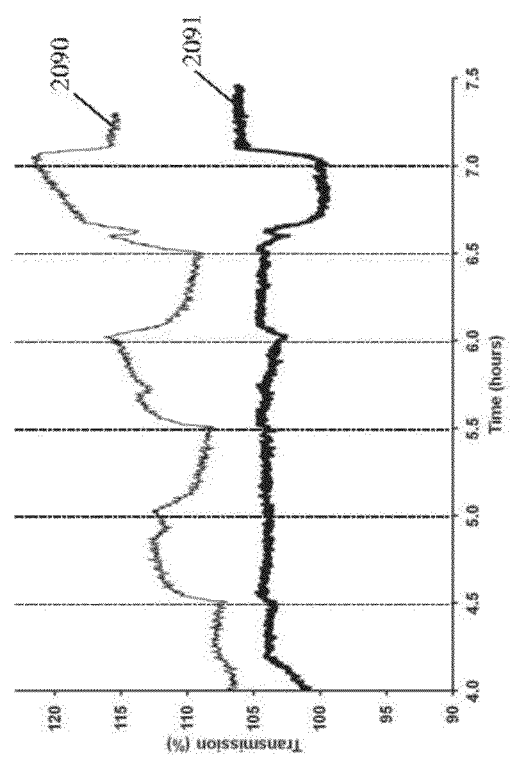
FIG. 20 illustrates a change in film transmittance at specific wavelengths for a highly scattering film with a root-mean squared surface roughness greater than 50 nm in response to a change in chemical composition.
Figure 19:
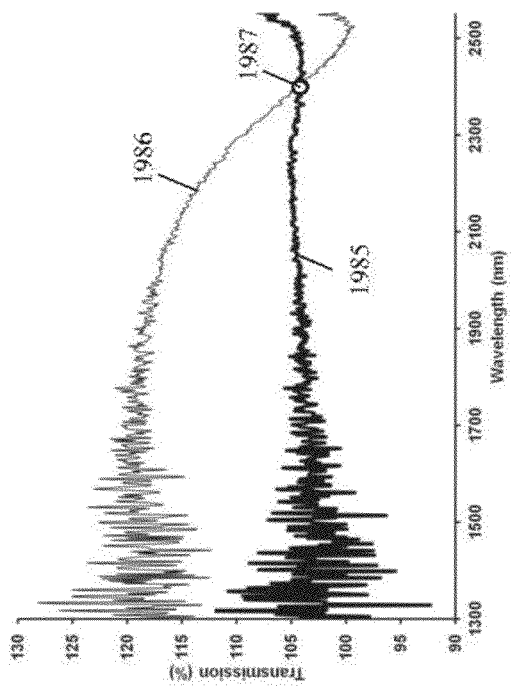
FIG. 19 illustrates a change in film transmittance of a highly scattering film with a root-mean squared surface roughness greater than 50 nm in response to a change in chemical composition.

FIGS. 17 and 18 illustrates simulated optical transmittance spectra of continuous 200 nm thick doped metal oxide films with two different degrees of rms surface roughness ($\sigma_{RMS}=0$ nm and $\sigma_{RMS}=50$ nm) using the same optical constants employed in generating FIG. 4 and FIG. 5 with a model that allows for surface roughness and the consequent light scattering to be explicitly accounted for. See e.g. J. M. Eastman, *Surface Scattering in Optical Interference Coatings*, PhD Thesis, U. of Rochester (1974). At FIG. 17 with a rms surface roughness $\sigma_{RMS}=0$ nm, trace 1780 represents specular transmission for a case where the carrier concentration $N=1\times10^{19}/cm^3$, while trace 1781 represents specular transmission for a case where the carrier concentration $N=5\times10^{19}/cm^3$. At FIG. 18 with a rms surface roughness $\sigma_{RMS}=50$ nm, trace 1880 represents specular transmission for a case where the carrier concentration $N=1\times10^{19}$, while trace 1881 represents specular transmission for a case where the carrier concentration $N=5\times10^{19}/cm^3$. It can be observed that an increased surface roughness is expected to change the shift in optical signal with increasing carrier concentration. Generally, increased surface roughness may cause a higher sensitivity of optical signal to changes in the real part of the dielectric constant of the doped metal oxide. This effect can result in a modified wavelength dependence of the optical signal shift and an enhancement in response over selected wavelengths. For example, FIG. 18 illustrates that the transmittance is observed to increase by approximately 10% at a wavelength of 1500 nm for a change in free carrier concentration from about $1\times10^{19}/cm^3$ (trace 1880) to about $5\times10^{19}/cm^3$ (trace 1881) when the rms surface roughness $\sigma_{RMS}=50$ nm, but a change cannot be clearly resolved for the smooth film of FIG. 17 for the same assumed change in free carrier density. Similarly in FIG. 18 an increase in transmission is predicted at 1800 nm for the rough film while a decrease is predicted for the smooth film of FIG. 17 for the same assumed change in free carrier concentration, resulting in a wavelength at which a cross-over in the sign of the optical signal response occurs. FIG. 19 illustrates experimentally measured transmittance spectra in the near-IR wavelength range for a 1% Al:ZnO film at 500° C. with rms surface roughness $\sigma_{RMS}$ greater than 50 nm, where trace 1985 indicates transmission in a gas atmosphere of $N_2$ and trace 1986 indicates transmission in a gas atmosphere of 4% $H_2$/Background N2. Traces 1985 and 1986 cross-over within the area 1987 indicated. Additionally, FIG. 20 indicates transmission spectra for the film of FIG. 19, where traces 2090 and 2091 occurs at a wavelengths of 2100 nm and 2500 nm respectively, and where the gas atmosphere from 4.5 to 5.0, 5.5 to 6.0, and 6.5 to 7.0 are 1% $H_2$, 2% $H_2$, and 4% $H_2$ respectively, with a background of $N_2$. Remaining time periods at FIG. 20 are with a gas atmosphere of $N_2$. These experimental spectra are consistent with the theoretical calculations of FIG. 18 due to the surface roughness showing a relatively large increase in transmission over a broad wavelength range from 1500-2300 nm as well as a decrease in transmission at 2500 nm. In an embodiment, the doped oxide material has an rms surface roughness of at least 15 nanometers. In some embodiments, the doped oxide material has an rms surface roughness of at least 50 nanometers.

In an embodiment, the change in the chemical composition of the monitored stream is an increased concentration of a reducing gas. Here, "reducing gas" means a gaseous constituent that alters the carrier concentration of the doped metal oxide comprising the doped oxide material as a result of contact between the gaseous constituent and the doped metal oxide. For example, when the doped metal oxide is an n-type oxide, the reducing gas might be expected to increase the carrier concentration. Exemplary reducing gases include $H_2$, CO, ammonia ($NH_3$), and hydrocarbons (e.g. fuel gases such as methane, ethane), among others. In another embodiment, the change in the chemical composition of the monitored stream is an increased concentration of an oxidizing gas, where "oxidizing gas" means a gaseous constituent altering the carrier concentration of the doped metal oxide comprising the doped oxide material as a result of contact between the gaseous constituent and the metal oxide. For example, when the doped metal oxide is an n-type oxide, the oxidizing gas might be expected to decrease the carrier concentration. Exemplary oxidizing gases include $O_2$, $O_3$, NOx, SOx, halogens (e.g. $F_2$, $Cl_2$, $Br_2$, and $I_2$), halogen compounds, sulfuric acids ($H_2SO_4$, $H_2S_2O_8$, and $H_2SO_5$), nitric acid and nitrate compounds, among others. The impact of a reducing or oxidizing gas on the carrier concentration of the doped metal oxide may be determined by any means known in the art, such as a Hall effect measurement. See e.g., Ramsden, Edward, *Hall Effect Sensors: Theory and Application*, ($2^{nd}$ Ed., 2006), among others.

The doped oxide material may be in the form of dispersed nanoparticles, an aggregate nanoparticle film, or a largely dense and continuous film. When the doped oxide material is the form of dispersed nanoparticles or an aggregate nanoparticle film, this means that a plurality of particles comprise the doped oxide material, and that some portion of the doped metal oxide comprising the doped oxide material comprises each particle in the plurality. In an embodiment, the plurality of nanoparticles has a Sauter mean diameter of less than 100 micron. The Sauter mean diameter may be determined by means known in the art. See e.g. Rhodes, Martin, *Introduction to Particle Technology* ($2^{nd}$ ed. 2008). Additionally, when the doped oxide material is in the form of dispersed nanoparticles, this means that the plurality of nanoparticles are sufficiently separated such that the plurality of nanoparticles displays an electrical conductance of less than $\frac{1}{10}$th of the electrical conductance of the metal oxide comprising the doped oxide material. Such a condition can be determined using various methods for the evaluation of proximity to a percolation limit in supported nanoparticle systems. See e.g. Trudeau et al., "Competitive transport and percolation in disordered arrays of molecularly linked Au nanoparticles," *J. Chem. Phys.*, Vol. 117 (2002), among others. Further, when the doped oxide material is in the form of an aggregate nanoparticle film, this means the plurality of nanoparticles displays an electrical conductance of at least $\frac{1}{10}$th of the electrical conductance of the metal oxide comprising the doped oxide material, and that a given volume containing the plurality of nanoparticles has a void fraction of at least 20%. Void fraction may be determined using means known in the art. See e.g., Yancey et al., "The influence of void space on antireflection coatings of silica nanoparticle self-assembled films," *J. Appl. Phys.* 99 (2006), and associated references. When the doped oxide material is in the form of a continuous film, this means that a given volume containing the doped oxide material has a void fraction of less than 20%. Additionally, it is understood that the nanoparticles of this disclosure are not limited to strictly spherical shapes, and that a plurality of nanoparticles may take shapes such as triangular prisms, disks, shells, wires, rods, and others.

The doped oxide material utilized in the method of this disclosure may be prepared using means known in the art for the production of dispersed nanoparticles, aggregate nanoparticle film, or a continuous films as disclosed herein. See e.g. Ohodnicki et al., "Plasmonic Transparent Conducting Metal Oxide Nanoparticles and Nanoparticle Films for Optical Sensing Applications," *Thin Solid Films* (2013), doi: 10.1016/j.tsf.2013.04.145, among others.

At FIG. 1, the monitored stream G is some portion of a gas stream. In an embodiment, the gas stream and the monitored stream are separated by a barrier layer, such as a dense filter layer to act as a diffusion barrier or a sieve material having an average pore size that is tailored to improve selectivity. Such an arrangement may be helpful when the gas stream is comprised of a molecular constituent which may need to be excluded from influencing the sensing operation. For example, a sieve material may be utilized to exclude the molecular constituent from the monitored stream by selecting a sieve material having an average pore size less than the molecular diameter of the molecular constituent to be excluded. Exemplary sieves include aluminosilicate minerals, clays, porous glasses, microporous charcoals, zeolites, active carbons, or synthetic compounds which display a standardized average pore size, such as pore size 3A, pore size 4A, etc. In a similar manner, the dense filter layer can be selected such that the diffusion of a species to be excluded is relatively sluggish. For example, exemplary filters might include films comprised of $SnO_2$, $SiO_2$, Palladium alloys, and others materials known for the selective filtering of hydrogen in an operation where the doped oxide material is utilized to detect changes in an $H_2$ concentration. An appropriately defined barrier layer can also protect the underlying gas oxide sensing material from the presence of particulates and undesirable corrosive species that may have a deleterious effect on long term stability of the gas oxide sensing material. In an embodiment, a first surface of the barrier material is contacted with the gas stream, and the monitored stream is withdrawn from a second surface of the barrier material.

Figure 15:
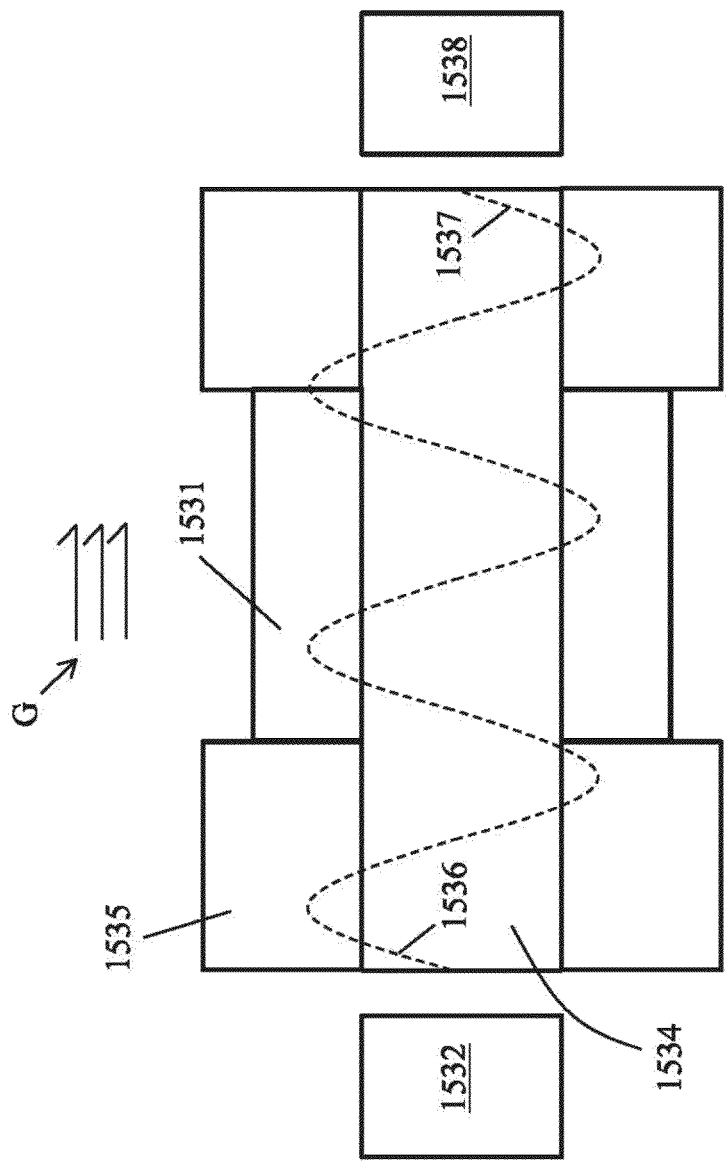
FIG. 15 illustrates a doped oxide material configuration suitable for the detection of changes to a chemical composition using a waveguide sensor.

In another embodiment, the doped oxide material is illuminated by a wave propagating along a waveguide, such as a fiber optic cable. This particular embodiment is illustrated at FIG. 15. The waveguide is comprised of a core material 1534 in contact with a cladding material 1535, where core material 1534 has a refractive index greater than cladding material 1535. For example, core material 1534 and cladding material 1535 may be comprised of silica and various additions such as germanium, titanium, phosphorous, boron, fluorine, or other dopants in order to alter the respective refractive indices and meet the necessary criteria. At FIG. 15 light source 1532 emits visible light into core material 1534, generating wave 1536 penetrating cladding material 1535. At FIG. 15, doped oxide material 1531 having the properties disclosed is placed in contact with core material 1534 such that doped oxide material 1531 is illuminated by wave 1536 as illustrated. Doped oxide material 1531 is additionally in contact with monitored stream G comprised of gaseous constituents. In an embodiment, monitored stream G has a temperature greater than about 200° C. Exiting light 1537 is collected by probe 1538. Interaction of doped oxide material 1531 with monitored stream G and illumination by wave 1536 enables detecting a change in the chemical composition of monitored stream G by detecting a shift in the optical signal, as earlier described.

Figure 16:
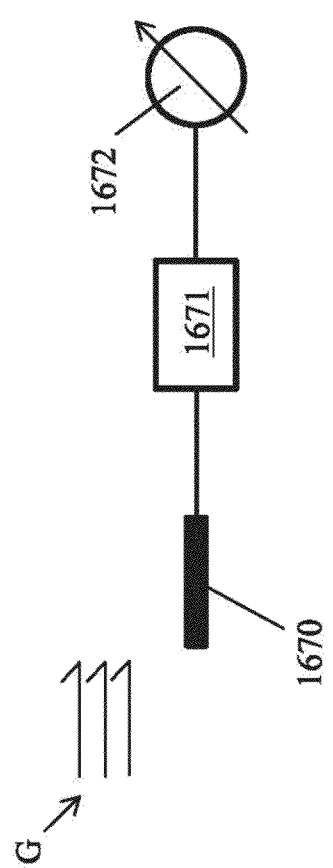
FIG. 16 illustrates an instrument utilizing the doped oxide material.

In another embodiment, the monotonic response of the doped oxide material displayed in response to increasing or decreasing concentrations of chemical species is utilized in a method of determining the concentration of a chemical species in a monitored stream. In this embodiment, the doped oxide material comprises a sensing head in a sensing instrument, where the sensing head communicates with an interrogator and a metered response is provided. The methodology is represented at FIG. 16, where the doped oxide material of this disclosure comprises sensing head 1670 in contact with monitored stream G. Monitored stream G is at a temperature greater than 100° C. and comprised of a chemical composition of gaseous constituents with concentrations varying over time. Interrogator 1671 illuminates the doped metal oxide comprising sensing head 1670 with incident light and gathers exiting light. Interrogator 1671 compares the incident light and the exiting light and generates a measurand, where the measurand is proportional to a shift in the optical signal as defined herein. Such interrogators for use in optical systems are known the art. See e.g., Lee et al., "Review of the present status of optical fiber sensors," *Optical Fiber Technology* 9 (2003), and associated references. Interrogator 1671 is in data communication with meter 1672 which provides an indication of the magnitude of the measurand generated and communicated by interrogator 1671. The monotonic response of the doped oxide material to increasing or decreasing concentrations of a chemical species in monitored stream G allows the measurand generated by interrogator 1671 and interpreted for display by meter 1672 to provide an indication of the concentration of the chemical species present. For example, utilizing the method illustrated at FIG. 16 for a monitored stream G experiencing the transient concentrations discussed for optical signal 816 at FIG. 8, a measurand generated by interrogator 1671 immediately prior to time $t_6$, where the monitored stream consists of 4% H2/N2 background, would have an absolute magnitude greater than a measurand generated by interrogator 1671 immediately prior to time $t_4$, where the monitored stream consists of 2% H2/N2 background. Correspondingly, the display provided by meter 1672 and noted at time $t_4$ and $t_6$ would serve as an indication of the differing magnitudes of the respective measurands, in this embodiment, the steps of illuminating the gas sensing oxide material, collecting exiting light, and monitoring an optical signal based on a comparison of the incident light and the exiting light is conducted by interrogator 1671, and detecting a shift in the optical signal is conducted through observation of meter 1672. An indication of the concentration of the chemical species present in monitored stream G is provided by comparison of the observed meter reading and a reference meter reading, where the reference meter reading results from a reference measurand generated under reference conditions, for example when monitored stream G consists solely of the background $N_2$, or some other condition.

Thus, provided here is a method for detecting a change in the chemical composition of monitored stream which utilizes changes in the optical signal generated by a doped oxide material. The doped oxide material comprises a metal oxide having a carrier concentration of at least $10^{18}/cm^3$, a bandgap of at least 2 eV, and an electronic conductivity of at least $10^1 S/cm$, at a temperature of 25° C. In an embodiment, the metal oxide is a doped metal oxide and M comprises at least a first element and a second element bonded with the oxygen anion. Exemplary doped metal oxides include but are not limited to AZO ($Zn_{1-x}Al_xO$) and ITO ($In_{2-x}Sn_xO_3$), Nb-doped TiO2 ($Ti_{1-x}Nb_xO_2$), and F-doped $SnO_2$. Changes in the chemical composition of a monitored stream in contact with the doped oxide material are detected based on a shift in the optical signal generated through comparison of incident and exiting light using optical spectroscopy, in a specific embodiment, the doped oxide material is illuminated by light propagating along a waveguide, such as a fiber optic core material. The method is particularly useful for monitoring the chemical composition of gaseous streams at elevated temperatures.

It is to be understood that the above-described arrangements are only illustrative of the application of the principles of the present invention and it is not intended to be exhaustive or limit the invention to the precise form disclosed. Numerous modifications and alternative arrangements may be devised by those skilled in the art in light of the above teachings without departing from the spirit and scope of the present invention. It is intended that the scope of the invention be defined by the claims appended hereto.

In addition, the previously described versions of the present invention have many advantages, including but not limited to those described above. However, the invention does not require that all advantages and aspects be incorporated into every embodiment of the present invention.

All publications and patent documents cited in this application are incorporated by reference in their entirety for all purposes to the same extent as if each individual publication or patent document were so individually denoted.

What is claimed is:

1. A method of a detecting a change in a chemical composition of a gas stream comprising:
    placing a doped oxide material in the gas stream, where the gas stream has a temperature of at least 100° C., and where the doped oxide material comprises a doped metal oxide, where the doped metal oxide has a carrier concentration of at least $10^{18}/cm^3$, a bandgap of at least 2 eV, and an electronic conductivity of at least $10^1$ S/cm at a temperature of 25° C.;
    contacting the doped metal oxide with a monitored stream, where the monitored stream is at least a portion of the gas stream, and where the monitored stream has a temperature of at least 100° C.;
    illuminating the doped metal oxide with a light source emitting incident light;
    collecting exiting light, where the exiting light is light that originates at the light source and is transmitted, reflected, scattered or a combination thereof by the doped metal oxide;
    monitoring an optical signal based on a comparison of the incident light and the exiting light using optical spectroscopy; and detecting a shift in the optical signal, thereby detecting the change in the chemical composition, and thereby monitoring the chemical composition of the gas stream.

2. The method of claim 1 where the doped metal oxide has an empirical formula $M_aO_b$ where M comprises one or more elements and where O comprises an oxygen anion.

3. The method of claim 2 where the doped metal oxide has an empirical formula $A_yB_xO_z$, where A is a first element and B is a second element.

4. The method of claim 3 where the first element, the second element, and the oxygen anion form a crystalline structure having a crystalline lattice, where the crystalline lattice is cubic, hexagonal, tetragonal, rhombohedral, orthorhombic, monoclinic, or triclinic, and where the first element, the second element, and the oxygen anion occupy special positions within crystalline lattice.

5. The method of claim 4 where the doped metal oxide comprises $Zn_{1-x}Al_xO_3$, $In_{2-x}Sn_xO_3$, $Ti_{1-x}Nb_xO_2$ or mixtures thereof.

6. The method of claim 2 where the gas stream has a temperature of at least 200° C., and where the monitored stream has a temperature of at least 200° C.

7. The method of claim 6 where the optical signal is a signal-averaged optical signal, and where the shift in the optical signal is detected when an observed signal-averaged optical signal is at least 0.1% greater or lesser than an initial signal-averaged optical signal.

8. The method of claim 6 where the change in the chemical composition is an increased concentration of a reducing gas, and where the shift in the optical signal is an increase in transmission at a specific wavelength.

9. The method of claim 6 where the exiting light has an optical signal edge between 250 and 550 nanometers, and where the shift in the optical signal comprises a shift in the optical signal edge.

10. The method of claim 6 where the exiting light has an optical signal edge between 1000 and 3750 nanometers, and where the shift in the optical signal comprises a shift in the optical signal edge, and where the change in the chemical composition is an increased concentration of a reducing gas, and where the shift in the optical signal edge is a shift to a lower wavelength.

11. The method of claim 6 where the doped oxide material has an rms surface roughness of at least 15 nanometers.

12. The method of claim 6 where the change in the chemical composition a change in the concentration of a reducing gas, where the reducing gas comprises $H_2$, CO, $NH_3$, a hydrocarbon, or mixtures thereof.

13. The method of claim 6 where the change in the chemical composition is a change in the concentration of an oxidizing gas, where the oxidizing gas comprises $O_2$, $O_3$, NOx, SOx, a halogen, a halogen compound, a sulfuric acid, a nitric acid, a nitrate, or mixtures thereof.

14. The method of claim 2 where the gas stream is comprised of a molecular gas constituent, and further comprising:
utilizing a barrier layer, where the barrier layer material has a first surface and a second surface, where the first surface and the second surface are separated by at least some portion of the barrier layer; and
contacting the first surface of the barrier layer and the gas stream, and withdrawing the monitored stream from the second surface of the barrier layer.

15. The method of claim 2 further comprising:
providing a waveguide comprised of a core material;
placing the doped oxide material in contact with the core material; and
emitting the incident light from the light source into the core material and illuminating the doped metal oxide, thereby illuminating the doped metal oxide with the light source emitting the incident light.

16. A method of determining a concentration of a chemical species in the monitored stream using the method of claim 1, further comprising:
placing a sensing head of an instrument in the monitored stream, where the doped oxide material comprises the sensing head and where the doped oxide material is in fluid communication with the monitored stream, thereby contacting the doped metal oxide with the monitored stream;
emitting incident light using an interrogator in optical communication with the doped oxide material comprising the sensing head and illuminating the doped oxide material, and gathering exiting light using the interrogator in optical communication with the doped oxide material, and comparing the optical signal based on a comparison of the incident light and the exiting light with optical spectroscopy using the interrogator, thereby illuminating the gas sensing oxide material with the light source emitting incident light, collecting exiting light, and comparing the incident light and the exiting light using optical spectroscopy;
generating a measurand using the interrogator based on the comparing the incident light and the exiting light, and communicating the measurand to a meter in data communication with the interrogator;
receiving the measurand at the meter and displaying a meter reading on the meter based on the measurand, and observing the meter reading, thereby generating an observed meter reading, and thereby monitoring the optical signal based the comparing the incident light and the exiting light;
evaluating a difference between the observed meter reading and a reference meter reading; and
assigning a value to the concentration of the chemical species in the monitored stream based on the difference between the observed meter reading and the reference meter reading, thereby determining the concentration of the chemical species in the monitored stream.

17. A method of a detecting a change in a concentration of a reducing gas in a gas stream comprising:
generating the gas stream, where the gas stream comprises the reducing gas, and where the gas stream has a temperature of at least 200° C.;
placing a doped oxide material in a gas stream, where the doped oxide material comprises a doped metal oxide, where the doped metal oxide has an empirical formula $M_aO_b$ where M comprises one or more elements and where O comprises an oxygen anion, and here the doped metal oxide has a carrier concentration of at least $10^{19}$/cm$^3$, a bandgap of at least 2 eV, and an electronic conductivity of at least $10^2$ S/cm at a temperature of 25° C.;
contacting the doped metal oxide with a monitored stream, where the monitored stream is at least a portion of the gas stream, and where the monitored stream comprises the reducing gas, and where the monitored stream has a temperature of at least 200° C.;
illuminating doped metal oxide with a light source emitting incident light;
collecting exiting light, where the exiting light is light that originates at the light source and is transmitted, reflected, or a combination thereof by the doped metal oxide;

monitoring an optical signal based on a comparison of the incident light and the exiting light using optical spectroscopy; and detecting a shift in the optical signal, thereby detecting the change in the concentration of the reducing gas in the gas stream.

18. The method of claim 17 where the doped metal oxide has an empirical formula $A_yB_xO_z$, where A is a first element and B is a second element, where the first element, the second element, and the oxygen anion form a crystalline structure having a crystalline lattice, where the crystalline lattice is cubic, hexagonal, tetragonal, rhombohedral, orthorhombic, monoclinic, or triclinic, and where the first element, the second element, and the oxygen anion occupy special positions within the crystalline lattice.

19. The method of claim 18 where the doped metal oxide is a non-stoichiometric oxide.

20. The method of claim 18 where the where doped metal oxide has a carrier concentration of at least $10^{19}/cm^3$, a bandgap of at least 2 eV, and an electronic conductivity of at least $10^2$ S/cm at a temperature of 25° C. following an elevated temperature reducing treatment, where the elevated temperature treatment comprises contacting the doped metal oxide for a period of at least one hour with a gaseous mixture having a composition of 4 vol. % $H_2$/balance $N_2$, where the gaseous mixture is at a temperature of at least 100° C.

* * * * *